US012735377B2

(12) United States Patent
Polishchuk et al.

(10) Patent No.: US 12,735,377 B2
(45) Date of Patent: Sep. 15, 2026

(54) SPIN ON METAL-ORGANIC FORMULATIONS

(71) Applicant: Merck Patents GmbH, Darmstadt (DE)

(72) Inventors: Orest Polishchuk, Bayonne, NJ (US); Takanori Kudo, Bedminster, NJ (US)

(73) Assignee: Merck Electronics KGAA, Darmstadt (DE)

(*) Notice: Subject to any disclaimer, the term of this patent is extended or adjusted under 35 U.S.C. 154(b) by 531 days.

(21) Appl. No.: 18/553,928

(22) PCT Filed: May 4, 2022

(86) PCT No.: PCT/EP2022/061946

§ 371 (c)(1),
(2) Date: Oct. 4, 2023

(87) PCT Pub. No.: WO2022/233919

PCT Pub. Date: Nov. 10, 2022

(65) Prior Publication Data

US 2025/0320174 A1 Oct. 16, 2025

Related U.S. Application Data

(60) Provisional application No. 63/185,235, filed on May 6, 2021.

(51) Int. Cl.
*C07C 39/15* (2006.01)
*C07C 69/017* (2006.01)

(52) U.S. Cl.
CPC ............ *C07C 39/15* (2013.01); *C07C 69/017* (2013.01)

(58) Field of Classification Search
CPC .... C23C 18/1295; C07C 39/15; C07C 69/017
See application file for complete search history.

(56) References Cited

U.S. PATENT DOCUMENTS

| | | | |
|---|---|---|---|
| 3,183,118 | A | 5/1965 | Conner |
| 3,419,587 | A | 12/1968 | Edward |
| 4,491,628 | A | 1/1985 | Ito et al. |
| 5,350,660 | A | 9/1994 | Urano et al. |
| 5,843,624 | A | 12/1998 | Houlihan et al. |
| 6,040,378 | A | 3/2000 | Sanduja et al. |
| 6,447,980 | B1 | 9/2002 | Rahman et al. |
| 6,723,488 | B2 | 4/2004 | Kudo et al. |
| 6,866,984 | B2 | 3/2005 | Jung et al. |
| 8,927,201 | B2 | 1/2015 | Takanashi et al. |
| 9,201,305 | B2 | 12/2015 | Rahman et al. |
| 9,274,426 | B2 | 3/2016 | Rahman et al. |
| 2012/0251956 | A1 | 10/2012 | Rahman et al. |

FOREIGN PATENT DOCUMENTS

| | | | |
|---|---|---|---|
| CN | 106502052 | A | 3/2017 |
| WO | 2022233919 | A2 | 11/2022 |
| WO | 2022233919 | A3 | 12/2022 |

OTHER PUBLICATIONS

Kogler et al_Polymer, Elsevier, Amsterdam, NL, Vo. 48, No. 17, Aug. 3, 2007, 4990-4995.
Kreutzer Johannes et al_European Journal of Inorganic Chemistry, vol. 2015, No. 17, Jun. 19, 2015, 2889-2894.
Mos R_B_et al_Journal of Analytical and Applied Pyrolysis, vol. 97, Sep. 1, 2012, 137-142.
Puchberger Michael et al_European Journal of Inorganic Chemistry, vol. 2006, No. 16, Aug. 1, 2006, 3283-3293.
Z. N. Pr ozor ovs kaya, et al._ Russian Journal of Inorganic Chemistry_1967, vol. 12 No. 10, 1348-1350.
International Search Report and Written Opinion received for International Application No. PCT/EP2022/061946, mailing date Nov. 21, 2022.
"International Preliminary Report on Patentability received for PCT Application No. PCT/EP2022/061946, mailing date Nov. 16, 2023", 18 Pages.

*Primary Examiner* — Sikarl A Witherspoon
(74) *Attorney, Agent, or Firm* — EMD Performance Materials Corp.; William T. Slaven, IV

(57) ABSTRACT

The disclosed and claimed subject matter relates to spin-on metal-organic formulations that include zirconium.

24 Claims, 11 Drawing Sheets

X-ray Diffractogram (XRD) pattern for Zirconium Propionate Polymorph S1 (ZPPA)

Results

| | | | Size (d.nm): | % Intensity: | St Dev (d.n... |
|---|---|---|---|---|---|
| Z-Average (d.nm): | 2.234 | Peak 1: | 2.561 | 100.0 | 1.034 |
| PdI: | 0.110 | Peak 2: | 0.000 | 0.0 | 0.000 |
| Intercept: | 0.650 | Peak 3: | 0.000 | 0.0 | 0.000 |
| Result quality : | Good | | | | |

Results

| | | | Size (d.nm): | % Intensity: | St Dev (d.n... |
|---|---|---|---|---|---|
| Z-Average (d.nm): | 8.668 | Peak 1: | 11.56 | 100.0 | 6.895 |
| PdI: | 0.225 | Peak 2: | 0.000 | 0.0 | 0.000 |
| Intercept: | 0.931 | Peak 3: | 0.000 | 0.0 | 0.000 |
| Result quality : | Good | | | | |

Figure 2. Structure of $[Zr_6O_4(OH)_4(OOCCH_2CH{=}CH_2)_{12}]_2$ (4).

SPIN ON METAL-ORGANIC FORMULATIONS

CROSS-REFERENCE TO RELATED APPLICATIONS

This application is a national stage application, filed under 35 U.S.C. § 371, of International Patent Application No. PCT/EP2022/061946 (filed on 4 May 2022) which claims the benefit of U.S. Provisional Patent Application No. 63/185,235 (filed on 6 May 2021) each of which applications is incorporated herein by reference in their entirety.

BACKGROUND

Field

The disclosed and claimed subject matter relates to a newly identified polymorph of zirconium (IV) propionate, spin-on metal-organic formulations including this new polymorph and the use thereof to form spin-on metal oxide hard masks.

Related Art

Metal oxide films are useful in a variety of applications in the semiconductor industry as lithographic hard masks and/or underlayers for anti-reflective coatings in electro-optical devices. In this regard, spin-on metal-organic formulations have been developed to replace CVD/PVD/ALD (Chemical Vapor Deposition/Physical Vapor Deposition/Atomic Layer Deposition) hard masks in the semiconductor manufacturing processes for the simplification of multiple stacks, their ability to allow for high throughput and their lower cost of ownership. Furthermore, the trend towards replacing planar NAND with 3D NAND has led to the development of new hard mask materials, in particular those enabling high aspect ratio etching. Spin-on metal oxide films provide excellent etch resistance in oxidative plasma and low Argon sputtering rates could be the excellent solution for lithographic patterning of multiple passes.

Underlayers containing high amounts of refractory elements can be used as hard masks (as well as antireflective coatings). Hard masks are useful when an overlying photoresist is not capable of providing high enough resistance to dry etching that is used to transfer the image into the underlying semiconductor substrate. In particular, such circumstances benefit from utilizing a hard mask whose etch resistance is high enough to transfer any patterns created over it into the underlying semiconductor substrate. This is made possible because the organic photoresist is different than the underlying hard mask and it is possible to find an etch gas mixture which will allow the transfer of the image in the photoresist into the underlying hard mask. This patterned hard mask can then be used with appropriate etch conditions and gas mixtures to transfer the image from the hard mask into the semiconductor substrate, a task which the photoresist by itself with a single etch process could not have accomplished. One approach has been to incorporate silicon, zirconium or other metallic materials into the hard mask layer underlayers, whereas other approaches utilize high carbon content layers (e.g., a trilayer of high carbon film/hard mask film/photoresist) to improve lithographic performance.

Conventional hard masks can be applied by vapor deposition techniques (e.g., CVD/PVD/ALD). However, as noted above, simpler application methodologies (e.g., spin coating) are desirable for depositing hard mask or antireflective coatings with high concentration of metallic materials.

Underlayer compositions for semiconductor applications containing metal oxides have been shown to provide dry etch resistance as well as antireflective properties. When higher concentrations of metal oxide are present in the underlayer, improved etch resistance and thermal conductance can be achieved. Conventional metal oxide compositions, however, have been found to be very unstable in air due to moisture and leading to issues with shelf-life stability, coating problems and performance shortcomings. Thus, there is an outstanding need to prepare spin-on hard mask, antireflective and other underlayers that contain high levels of stable soluble metal oxides which are soluble or colloidally stable.

The use of zirconium (IV) precursors in spin-on formulations/coatings is well known in the art. For example, U.S. Pat. No. 9,201,305 describes how to formulate zirconium oxide propionate, zirconium acetate, zirconium (IV) oxide 2-ethylhexanoate and zirconium (IV) acetyacetonate with crosslinkable polymers (with or without wetting agents), surfactants, anti-foam agents etc., in organic solvents such as PGME, PGMEA or ArF Thinner to make spin on compositions.

Given the performance of such zirconium (IV) precursors, an objective of the present research was to identify new zirconium (IV) precursors in spin-on formulations. As noted above, the disclosed and claimed subject matter relates to a newly identified polymorph of zirconium (IV) propionate and its use in spin-on hard mask formulations.

There are other known zirconium (IV) propionate materials other than the new materials described herein. For example, the *Russian Journal of Inorganic Chemistry,* 12 (10) p. 1348-1350 (1967) describes the following reaction:

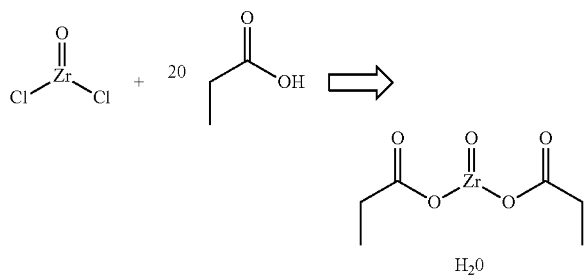

in which the predicted tetrameric structure of the zirconium oxo-propionate product is as shown in FIG. 8.

In the *Eur. J. Inorg. Chem.,* 3283-3293 (2006), the authors describe the synthesis of $[Zr_6O_4(OH)_4(OOCCH2Me)_{12}]_2 \cdot 6MeCH_2COOH$ with the structure as shown in FIG. 9.

The *Journal of Analytical and Applied Pyrolysis,* 97, 137-142 (2012) the reaction of zirconium(IV) acetylacetonate and propionic acid to form $[Zr_6O_4(OH)_4(CH_3CH_2COO)_{12}]_2 \cdot 11H_2O$ having the structure shown in FIG. 10.

Notwithstanding the above, there remains a need for zirconium (IV) propionate compounds and formulations thereof suitable for use spin-on applications that produce robust ZrOx films. The present disclosure addresses these needs.

SUMMARY

In one embodiment, the disclosed and claimed subject matter relates to zirconium propionate polymorph S1 ("ZPPA"), the features of which are described in more detail below.

In another embodiment, the disclosed and claimed subject matter relates to a method for synthesizing ZPPA. In a further aspect of this embodiment, ZPPA is prepared by reacting zirconium(IV)(tert-butoxide)$_4$ with propionic anhydride and propionic acid, 3:1 molar ratio, and then reacting the same with propylene glycol monomethyl ether (PGME) in a solvent free environment.

In another embodiment, the disclosed and claimed subject matter relates to formulations and the preparation thereof that include ZPPA or zirconium (IV) propionate ("ZPP"). In a further aspect of this embodiment, the formulations include other additives useful for managing the properties of post baked films in lithography.

In one embodiment, the formulations include (i) ZPP and/or ZPPA, (ii) one or more etch resistance modulator additive and (iii) one or more solvents. In others embodiment, the formulations further include one or both of (iv) one or more surfactant and (v) one or more water resistivity enhancer.

In another embodiment, the disclosed and claimed subject matter relates to use of formulations of ZPP and/or ZPPA to form highly crosslinked ZrOx films on a substrate under thermal decomposition. In a further aspect, the ZrOx films exhibit etch resistivity of greater than approximately 0.1 Å/sec and/or Ar sputtering rates of lower than approximately 20 Å/sec. In a further aspect, the ZrOx films exhibit etch resistivity of greater than approximately 0.1 Å/sec and/or Ar sputtering rates of lower than approximately 10 Å/sec. In a further aspect, the ZrOx films exhibit etch resistivity of greater than approximately 10 Å/sec to approximately 20 Å/sec. In a further aspect, the ZrOx films exhibit etch resistivity of greater than approximately 5 Å/sec to approximately 20 Å/sec. In a further aspect, the ZrOx films exhibit etch resistivity of greater than approximately 5 Å/sec to approximately 15 Å/sec.

The disclosed and claimed subject matter also pertains to the process using the aforementioned ZPP and/or ZPPA formulations to fill (e.g., "gap fill") lithographic features on a substrate which, after processing, yield a substrate comprising a patterned high ZrOx film.

Specifically, the disclosed and claimed subject matter further relates to using these novel air stable compositions of ZPP and/or ZPPA to coat a patterned substrate which is a patterned photoresist, patterned spin on carbon, or patterned semiconductor comprising, vias, trenches, holes or other hollow topographical features patterns filling these voids with low void formation and using these filled patterns in a process to form a patterned ZrOx film on the substrate.

This summary section does not specify every embodiment and/or incrementally novel aspect of the disclosed and claimed subject matter. Instead, this summary only provides a preliminary discussion of different embodiments and corresponding points of novelty over conventional techniques and the known art. For additional details and/or possible perspectives of the disclosed and claimed subject matter and embodiments, the reader is directed to the Detailed Description section and corresponding figures of the disclosure as further discussed below.

The order of discussion of the different steps described herein has been presented for clarity sake. In general, the steps disclosed herein can be performed in any suitable order. Additionally, although each of the different features, techniques, configurations, etc. disclosed herein may be discussed in different places of this disclosure, it is intended that each of the concepts can be executed independently of each other or in combination with each other as appropriate. Accordingly, the disclosed and claimed subject matter can be embodied and viewed in many different ways.

BRIEF DESCRIPTION OF THE DRAWINGS

The accompanying drawings, which are included to provide a further understanding of the disclosed subject matter and are incorporated in and constitute a part of this specification, illustrate embodiments of the disclosed subject matter and together with the description serve to explain the principles of the disclosed subject matter. In the drawings.

DEFINITIONS

Figure 1:
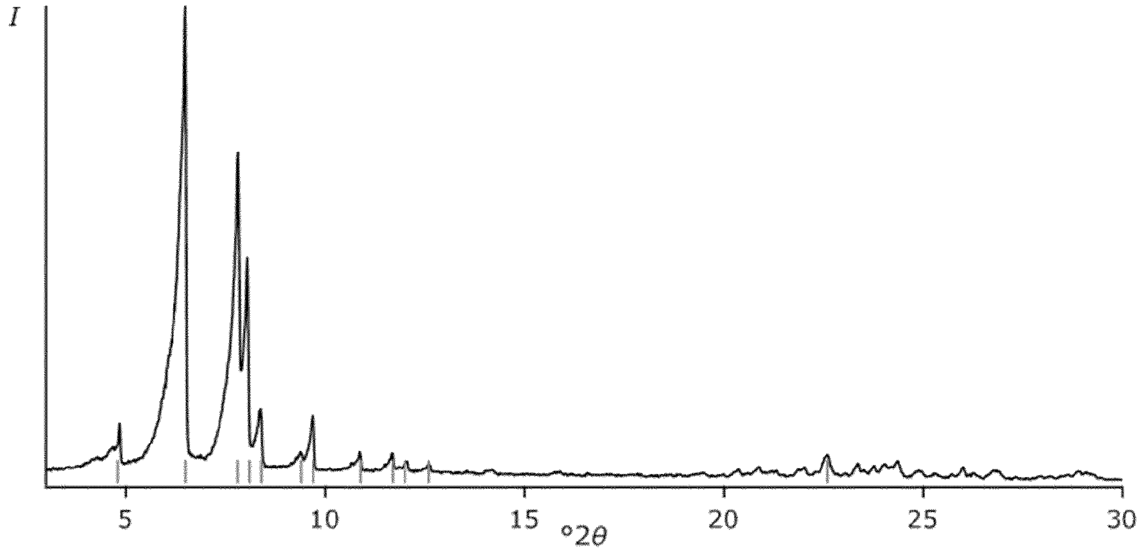
FIG. 1 illustrates the powder X-ray diffractogram (XRD) pattern for zirconium propionate polymorph S1 (ZPPA)

Unless otherwise stated, the following terms used in the specification and claims shall have the following meanings for this application.

In this application, the use of the singular includes the plural, and the words "a," "an" and "the" mean "at least one" unless specifically stated otherwise. Furthermore, the use of the term "including," as well as other forms such as "includes" and "included," is not limiting. Also, terms such as "element" or "component" encompass both elements or components including one unit and elements or components that include more than one unit, unless specifically stated otherwise. As used herein, the conjunction "and" is intended to be inclusive and the conjunction "or" is not intended to be exclusive, unless otherwise indicated. For example, the phrase "or, alternatively" is intended to be exclusive. As used herein, the term "and/or" refers to any combination of the foregoing elements including using a single element.

The term "about" or "approximately," when used in connection with a measurable numerical variable, refers to the indicated value of the variable and to all values of the variable that are within the experimental error of the indicated value (e.g., within the 95% confidence limit for the mean) or within percentage of the indicated value (e.g., ±10%, ±5%), whichever is greater.

As used herein, "$C_{x-y}$" designates the number of carbon atoms in a chain. For example, $C_{1-6}$ alkyl refers to an alkyl chain having a chain of between 1 and 6 carbons (e.g., methyl, ethyl, propyl, butyl, pentyl and hexyl). Unless specifically stated otherwise, the chain can be linear or branched.

Unless otherwise indicated, "alkyl" refers to hydrocarbon groups which can be linear, branched (e.g., methyl, ethyl, propyl, isopropyl, tert-butyl and the like), cyclic (e.g., cyclohexyl, cyclopropyl, cyclopentyl and the like) or multicyclic (e.g., norbornyl, adamantyl and the like). Suitable acyclic groups can be methyl, ethyl, n- or iso-propyl, n-, iso-, or tert-butyl, linear or branched pentyl, hexyl, heptyl, octyl, decyl, dodecyl, tetradecyl and hexadecyl. Unless otherwise stated, alkyl refers to 1-10 carbon atom moieties. The cyclic alkyl groups may be mono-cyclic or polycyclic. Suitable examples of mono-cyclic alkyl groups include substituted cyclopentyl, cyclohexyl, and cycloheptyl groups. The substituents may be any of the acyclic alkyl groups described herein.

"Alkoxy" (a.k.a. "alkyloxy") refers to an alkyl group as defined above which is attached through an oxy (—O—) moiety (e.g., methoxy, ethoxy, propoxy, butoxy, 1,2-isopropoxy, cyclopentyloxy, cyclohexyloxy and the like). These alkoxy moieties may be substituted or unsubstituted.

"Alkyl carbonyl" refers to an alkyl group as defined above which is attached through a carbonyl group (—C(═O—)) moiety (e.g., methylcarbonyl, ethylcarbonyl, propylcarbonyl, buttylcarbonyl, cyclopentylcarbonyl and the like). These alkyl carbonyl moieties may be substituted or unsubstituted.

"Hydroxy" (a.k.a. "hydroxyl") refers to an —OH group.

Unless otherwise indicated, the term "substituted" when referring to an alkyl, alkoxy, fluorinated alkyl and the like refers to one of these moieties which also contains one or more substituents including, but not limited, to the following substituents: alkyl, substituted alkyl, unsubstituted aryl, substituted aryl, alkyloxy, alkylaryl, haloalkyl, halide, hydroxy, amino and amino alkyl. Similarly, the term "unsubstituted" refers to these same moieties where no substituents apart from hydrogen are present.

Alkylene groups are divalent alkyl groups derived from any of the alkyl groups mentioned hereinabove. When referring to alkylene groups, these include an alkylene chain substituted with ($C_1$-$C_{18}$) alkyl groups in the main carbon chain of the alkylene group. Alkylene groups can also include one or more alkyne groups in the alkylene moiety, where alkyne refers to a triple bond. Essentially an alkylene is a divalent hydrocarbon group as the backbone. Accordingly, a divalent acyclic group may be methylene, 1,1- or 1,2-ethylene, 1,1-, 1,2-, or 1,3 propylene, 2,5-dimethylhexene, 2,5-dimethyl-hex-3-yne, and so on. Similarly, a divalent cyclic alkyl group may be 1,2- or 1,3-cyclopentylene, 1,2-, 1,3-, or 1,4-cyclohexylene, and the like. A divalent tricyclo alkyl groups may be any of the tricyclic alkyl groups mentioned herein above. An example of a tricyclic alkyl group is 4,8-bis(methylene)-tricyclo[5.2.1.0.$^{2,6}$]decane. When referring to a perfluoroalkylene these include materials describe above as alkylene group but in which the hydrogen atoms have been replaced by fluorine. Similarly, when describing a partially fluorinated alkylene group this is an alkylene group in which part of the hydrogen atoms have been replaced by fluorine.

Aryl groups contain 6 to 24 carbon atoms including phenyl, tolyl, xylyl, naphthyl, anthracyl, biphenyls, bis-phenyls, tris-phenyls and the like. These aryl groups may further be substituted with any of the appropriate substituents e.g. alkyl, alkoxy, acyl or aryl groups mentioned hereinabove. Similarly, appropriate polyvalent aryl groups as desired may be used in this disclosed and claimed subject matter. Representative examples of divalent aryl groups, arylene, include phenylenes, xylylenes, naphthylenes, biphenylenes, and the like. As used herein, and unless otherwise specified, the term "aromatic" refers to unsaturated cyclic hydrocarbons having a delocalized conjugated $\pi$ system and having from 4 to 20 carbon atoms (aromatic $C_4$-$C_{20}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. The aromatic may optionally be substituted, e.g., with one or more alkyl group, alkoxy group, halogen, etc. For example, the aromatic may include anisole. Additionally, the aromatic may comprise one or more heteroatoms. Examples of heteroatoms include, but are not limited to, nitrogen, oxygen, phosphorus, boron, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

The term "non-aromatic" means four or more carbon atoms joined in at least one ring structure wherein at least one of the four or more carbon atoms in the ring structure is not an aromatic carbon atom.

The term (meth)acrylate refers to methacrylate or acrylate, and similarly, (meth)acrylic refers to methacrylic or acrylic.

The concentration of the organic polymer and the zirconate compound, based on total solids, can vary depending on the zirconium content required in the final underlayer film. The concentration of the zirconium in the composition and the curing process can determine the final zirconium content of the cured film. The concentration of the organic polymer in the novel composition can vary from about 0.1 weight % to about 90 weight % based on total solids; the concentration of the zirconate compound can vary from about 10 weight % to about 99.9 weight % based on total solids. As an example, for nonpolymeric zirconates, the concentration can range from about 10 weight % to about 50 weight % of total solids. For polymeric/oligomeric zirconates, the concentration can range from about 10 weight % to about 99.9 weight % of total solids, or 50-97 weight %. Mixtures of the nonpolymeric and polymeric zirconates may be also be used.

The zirconium content of the cured film can range from about 3-80 weight % or about 10-70 weight % or about 20-60 weight % after a 250° C. cure, as measured by elemental analysis. The curing conditions determine the zirconium content of the film, the higher the curing temperature and/or longer the curing time the higher the zirconium content.

In the embodiment of the present disclosed and claimed subject matter where the underlayer may also act as an antireflective layer, that is, sufficient chromophore groups are present, the refractive indices of the underlayer, n (refractive index) can range from about 1.4 to about 2.7 for the refractive index and k (absorption) can range from about 0.1 to about 0.7 at 193 nm exposure wavelength. The novel film is useful as an antireflective coating at this wavelength and as a hard mask. The n and k values can be calculated using an ellipsometer, such as the J. A. Woollam VUV-VASE VU-32™ Ellipsometer. The exact values of the optimum ranges for k and n are dependent on the exposure wavelength used and the type of application. Typically for 193 nm the preferred range for k is about 0.1 to about 0.6, and for 248 nm the preferred range for k is about 0.03 to about 0.8.

The composition of the disclosed and claimed subject matter may contain 1 weight % to about 50 weight % of the total solids in the solution, or 2 weight % to 30 weight % of the total solids in the solution. The solid components of the underlayer coating composition are mixed with a one solvent or mixtures of one or more solvents that dissolve the solid components of the antireflective coating. Suitable solvents may include, for example, lower alcohols ($C_1$-$C_6$) such as isopropanol, n-butanol, t-butanol, 1-pentanol and 4-methyl-2-pentanol, a glycol such as ethylene glycol and propylene glycol, a glycol ether derivative such as ethyl cellosolve, methyl cellosolve, propylene glycol monomethyl ether, diethylene glycol monomethyl ether, diethylene glycol monoethyl ether, dipropylene glycol dimethyl ether, propylene glycol n-propyl ether, or diethylene glycol dimethyl ether; a glycol ether ester derivative such as ethyl cellosolve acetate, methyl cellosolve acetate, or propylene glycol monomethyl ether acetate; carboxylates such as ethyl acetate, n-butyl acetate and amyl acetate; carboxylates of di-basic acids such as diethyloxylate and diethylmalonate; dicarboxylates of glycols such as ethylene glycol diacetate and propylene glycol diacetate; and hydroxy carboxylates such as methyl lactate, ethyl lactate, ethyl glycolate, and ethyl-3-hydroxy propionate; a ketone ester such as methyl pyruvate or ethyl pyruvate; an alkoxy alcohol such as 2-methoxyethanol, ethoxyethanol, an alkoxycarboxylic acid ester such as methyl 3-methoxypropionate, ethyl 3-ethoxypropionate, ethyl 2-hydroxy-2-methylpropionate, or methylethoxypropionate; a ketone derivative such as methyl ethyl ketone, acetyl acetone, cyclopentanone, cyclohexanone or 2-heptanone; a ketone ether derivative such as diacetone alcohol methyl ether; a ketone alcohol derivative such as acetol or diacetone alcohol; lactones such as butyrolactone and gamma-valaro lactone; an amide derivative such as dimethylacetamide or dimethylformamide, anisole, and mixtures thereof.

Other components may be added to enhance the performance of the coating, e.g., lower alcohols ($C_1$-$C_6$ alcohols), alkoxyalcohols, lactones, $C_1$-$C_{20}$ alkyl carboxylic acids, surface leveling agents (<5 weight % of total solids), dialkoxy bis(betadiketoesters) (1-20 weight % or 5-10 weight % of total solids), dialkoxy bis(beta diketone) (1-20 weight % or 5-10 weight % of total solids), thermal acid generator, photoacid generator, etc. Examples of dialkoxy bis(betadiketoesters) and dialkoxy bis(beta diketone) can be acetylacetone, benzoylacetone, 4,4,4-Trifluoro-1-phenyl-1, 3-butanedione, and ethyl acetoacetate Surface leveling agents or surfactants can be nonionic, cationic or anionic surfactants, such as polyoxyalkylene ether based surfactants, fluoroalkyl based surfactant and silicone based surfactants.

When referring to compositions of ZPP and/or ZPPA described herein in terms of weight % (wt %), it is understood that in no event shall the weight % of all components, including non-essential components, such as impurities, add to more than 100 weight %. In compositions "consisting essentially of" recited components, such components may add up to 100 weight % of the composition or may add up to less than 100 weight %. Where the components add up to less than 100 weight %, such composition may include some small amounts of a non-essential contaminants or impurities. For example, in one such embodiment, a ZPP or ZPPA formulation can contain 2% by weight or less of impurities. In another embodiment, a ZPP or ZPPA formulation can contain 1% by weight or less than of impurities. In a further embodiment, a ZPP or ZPPA formulation can contain 0.05% by weight or less than of impurities. In other such embodiments, the constituents can form at least 90 wt %, more preferably at least 95 wt %, more preferably at least 99 wt %, more preferably at least 99.5 wt %, most preferably at least 99.9 wt %, and can include other ingredients that do not material affect the performance of the wet etchant. Otherwise, if no significant non-essential impurity component is present, it is understood that the composition of all essential constituent components will essentially add up to 100 wt %.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that any of the incorporated literature and similar materials defines a term in a manner that contradicts the definition of that term in this application, this application controls.

DETAILED DESCRIPTION

It is to be understood that both the foregoing general description and the following detailed description are illustrative and explanatory, and are not restrictive of the subject matter, as claimed. The objects, features, advantages and ideas of the disclosed subject matter will be apparent to those skilled in the art from the description provided in the specification, and the disclosed subject matter will be readily practicable by those skilled in the art on the basis of the description appearing herein. The description of any "preferred embodiments" and/or the examples which show preferred modes for practicing the disclosed subject matter are included for the purpose of explanation and are not intended to limit the scope of the claims.

It will also be apparent to those skilled in the art that various modifications may be made in how the disclosed and claimed subject matter is practiced based on described aspects in the specification without departing from the spirit and scope of the disclosed subject matter disclosed herein.

As set forth above, the disclosed and claimed subject matter relates to (i) to zirconium propionate polymorph S1 ("ZPPA"), (ii) methods of preparing ZPPA, (iii) formulations including ZPP and/or ZPPA and (iv) the formation of ZrOx films from formulations of ZPP and/or ZPPA.

I. Zirconium Propionate Polymorph S1 (ZPPA)

In one aspect, the disclosed and claimed subject matter relates to zirconium propionate polymorph S1 ("ZPPA") and a method of preparing the same.

A. ZPPA Molecule

Figure 11:
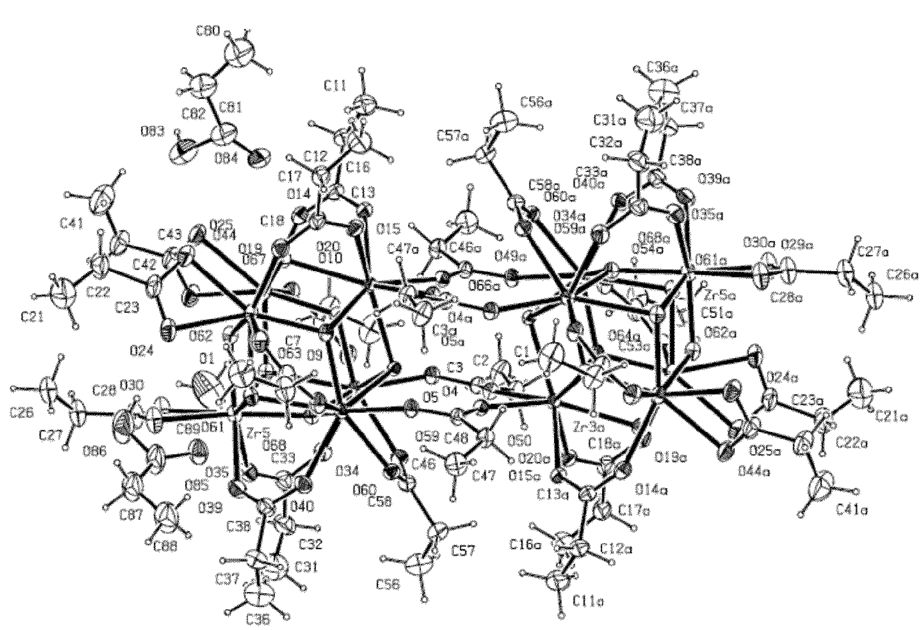
FIG. 11 illustrates the crystal structure of the zirconium propionate polymorph S1 (ZPPA).

ZPPA has been shown to have the formula $C_{72}H_{128}O_{64}Zr_{12}\times 4(C_3H_5O_2)\times 2(H_2O)$ and the structure as shown in FIG. 11.

B. Characterization of ZPPA

Table 1 below sets forth the properties of ZPPA.

TABLE 1

| | |
|---|---|
| Empirical formula | $C_{72}H_{128}O_{64}Zr_{12}$ $4 \times C_3H_5O_2$ $2 \times H_2O$ |
| Molecular weight | 3444.72⁹/mol |
| Diffractometer/Detector | SuperNova (Agilent), Atlas CCD Detector |
| Radiation | Cu Kα (1.5418 Å), X-ray mirrors |
| Crystal size | (0.111 × 0.105 × 0.044) $mm^3$ |
| Temperature | 298 K |
| Diffraction Experiment ID | exp_3537 |
| Crystal system | monoclinic |
| Space group | 12/a |
| Lattice parameters: | |
| a, b, c | 17.4006(7) Å, 21.9079(8) Å, 36.4944(13) Å |
| α, β, γ | 90°, 95.235(4)°, 90° |
| Unit cell volume | 13854.0(9) $Å^3$ |
| Formula units per unit cell | 4 |
| F(000) | 6192 |
| Calculated density | 1.479⁹/$cm^3$ |
| Linear absorption coeff. | 7.806 $mm^{-1}$ |
| Scan | ω-scans |
| Measured reflections | 21314 |
| Index limits | −19 ≤ h ≤ 18; −24 ≤ k ≤ 23; −27 ≤ l ≤ 41 |
| $R_{int}$ (internal consistency of the dataset) | 0.0252 |
| Reflections used | 10124 |
| Refined parameters/restraints | 800/6 |
| R1 (1 > 2α) | 0.0589 |
| $wR^2$ (all data) | 0.2001 |
| GooF S | 1.055 |
| Max. shift in final cycle | ≤5.060 |
| Max./min. differential electron density | max: 1.155/min: −0.773 $e^-/Å^3$ |
| Structure Solution/Refinement | SHELK-97; G.M. Sheldrick, *Acta Cryst. A*, 64, 2008, 112 G.M. Sheldrick, Univ. Göttingen, 1997. |
| Automated Report | Olex2.1.2 2017 Feb. 23 svn.r3390 for OlexSys |

As shown in Table 1, ZPPA has a molecular weight of 3447.72 g/mol.

FIG. 1 illustrates the powder X-ray diffractogram (XRD) for ZPPA. As shown in FIG. 1, ZPPA has characteristic peaks at approximately 4.8, 6.5, 7.8, 8.1, 8.4, 9.4, 9.7, 10.9, 11.7, 12.0, 12.6 and 22.6±0.2 degrees of 2θ.

Figure 2:
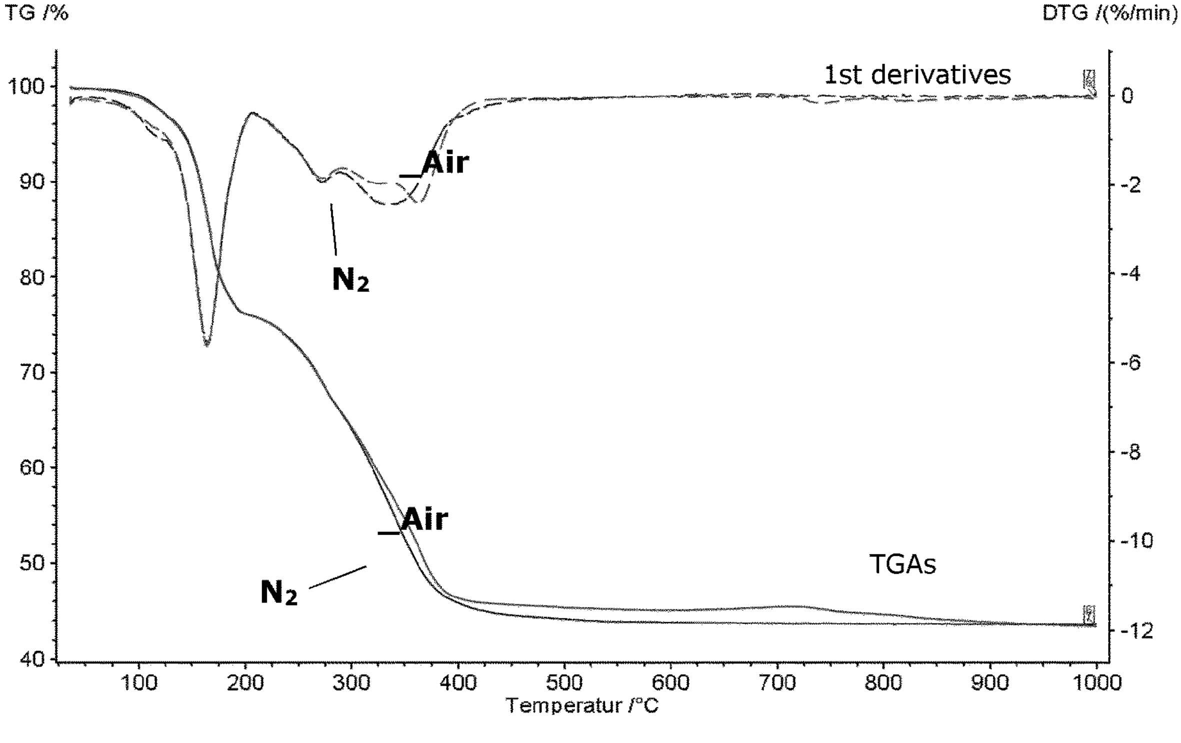
FIG. 2 illustrates the Thermo Gravimetric Analyses (TGA) of ZPPA prepared in Example 1.
Figure 3:
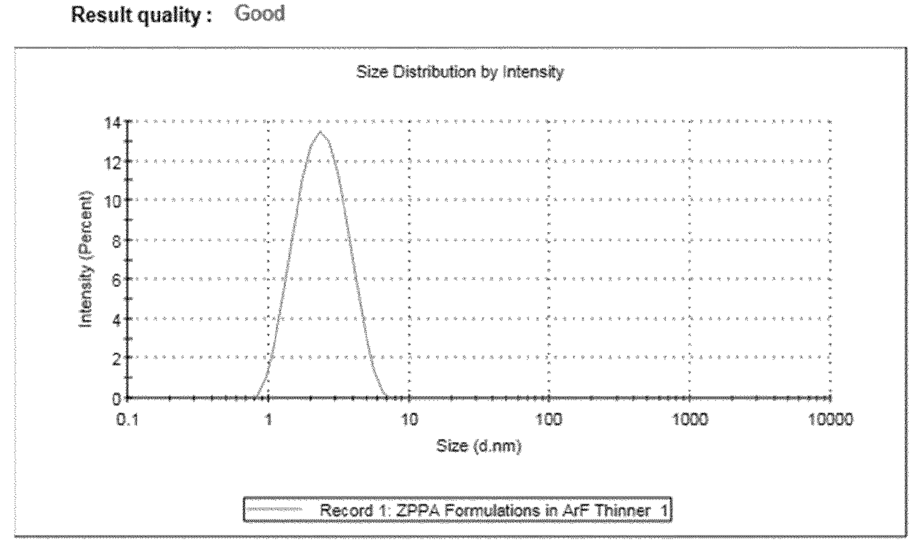
FIG. 3 illustrates the Dynamic Light Scattering (DLS) analysis of the ZPPA formulation in Example 1.

FIG. 2 illustrates the TGA analysis of ZPPA prepared in Example 1. As shown in FIG. 2, the thermal behavior of the material under air and inert conditions is identical up to a temperature of approximately 300° C. The mass loss at >300° C. shows different temperatures at the minima of the first derivative, which means that the process must be different. In addition, an increase in mass is detected at approximately 800'° C. This can be attributed to a possible oxidation. The residual mass after 1000° C. can be regarded as identical for both measurements.

II. ZPP

Zirconium propionate ("ZPP") is a white powder with a complex structure generally believed to be based on hydroxy-bridged zirconium polymers with the propionate carboxyl group bonded to the zirconium. Although ZPP with the CAS No. 84057-80-7 is described as $Zr(CH_3CH_2COO)_4$, ZPP can be hydrolyzed and may exist in combination with one of several hydrolyzed/protonated species of formula $Zr(CH_3CH_2COO)_{4-x}(OH)_x$, where x=1-3. Moreover, ZPP can also exist in oligomeric or polymeric forms that contain repeat units of the various hydrolyzed species (i.e., Table 2 where there are between 1 and 3 propionates bonded to each zirconium) coupled to one another by bridging hydroxyl groups. Such oligomeric or polymeric forms can also exist as mixtures in combination with various of the monomeric species (e.g., $Zr(CH_3CH_2COO)_4$).

TABLE 2

| | Free Monomer Species<br>1 | Protonated (Bridging) Species<br>2 | Repeat Unit<br>3 |
|---|---|---|---|
| A | 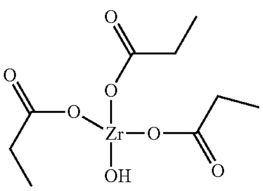<br>x = 1<br>Mw = 327.4<br>Elemental Analysis: C, 33.01;<br>H, 4.93; O, 34.20; Zr, 27.86 | 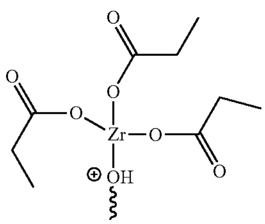<br>1 x $CH_3CH_2COO^-$ | 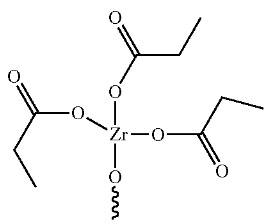 |
| B | 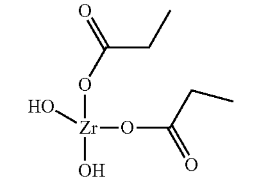<br>x = 2<br>Mw = 271.38<br>Elemental Analysis: C, 26.56;<br>H, 4.46; O, 35.37; Zr, 33.61 | 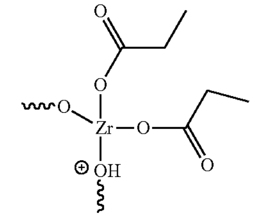<br>1 x $CH_3CH_2COO^-$ | 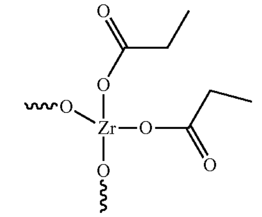 |
| C | 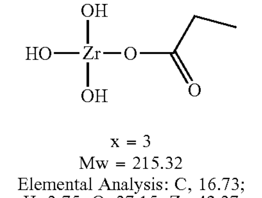<br>x = 3<br>Mw = 215.32<br>Elemental Analysis: C, 16.73;<br>H, 3.75; O, 37.15; Zr, 42.37 | 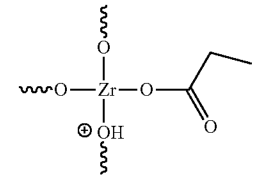<br>1 x $CH_3CH_2COO^-$ | 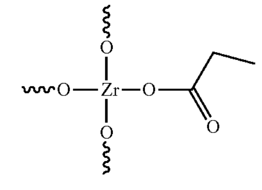 |
| D | 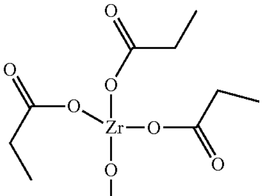<br>x = 0<br>Mw = 383.51<br>Elemental Analysis: C, 37.58;<br>H, 5.26; O, 33.37; Zr, 23.79 | 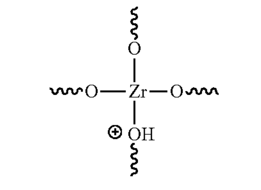<br>1 x $CH_3CH_2COO^-$ | 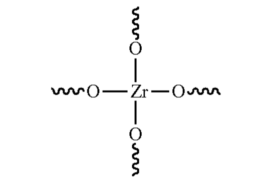 |

In Table 2, "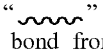" represents an actual or potential direct valence bond from a protonated or unprotonated oxygen atom to another zirconium in an oligomer or polymeric zirconium complex, or alternatively a direct valence bond to H forming a Zr—OH moiety (i.e., that can also exist in equilibrium with free propionate groups or propionic acid molecules). Thus, the oligomer or polymeric species include linking/bridging moieties Zr—$(OH)^+$—Zr and/or Zr—(O)—Zr and such oligomeric or polymeric species may also include, structurally, combinations of these linking moieties present along with some free ZrOH moieties.

In one embodiment, the ZPP as used herein includes a monomer. In one embodiment, the ZPP as used herein includes an oligomer or polymeric species (or a mixture thereof) where the ZPP is about a 10-mer to about a 15-mer. In one embodiment, the ZPP as used herein includes an oligomer or polymeric species (or a mixture thereof) having an Mw of about a 10-mer to about a 15-mer of ZPP. In another embodiment, the ZPP has an average molecular weight of about 4,000 Da to about 10,000 Da.

In one embodiment, the ZPP as used herein includes an oligomer or polymeric species (or a mixture thereof) including, in any sequence, the repeat units (where the monomer is defined by the structure in Table 2 corresponding to the letter of the respective row and the number of the respective column, e.g. A2 corresponds to structure in row A column 2):

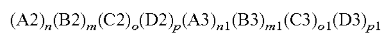

$$(A2)_n(B2)_m(C2)_o(D2)_p(A3)_{n1}(B3)_{m1}(C3)_{o1}(D3)_{p1}$$

where each of n, n1, m, m1, o, o1, p and p1=0-10 and the total of n, n1, m, m1, o, o1, p and p1 is between 2 and 10. In a further aspect of this embodiment, the ZPP oligomeric and/or polymeric species constitute a mixture with one or more of ZPP monomer species A1, B1, C1 and D1. In a further aspect of this embodiment, n=0. In a further aspect of this embodiment, m=0. In a further aspect of this embodiment, o=0. In a further aspect of this embodiment, m=0. In a further aspect of this embodiment, p=0. In a further aspect of this embodiment, n1=0. In a further aspect of this embodiment, m1=0. In a further aspect of this embodiment, o1=0. In a further aspect of this embodiment, m1=0. In a further aspect of this embodiment, p1=0. In a further aspect of this embodiment, the ZPP oligomeric and/or polymeric species will include one of A2 and A3 species in a terminal chain position(s).

In one embodiment, the ZPP includes an oligomer or polymeric species that includes repeat units derived from free monomer species B1 and C1. In a further aspect of this embodiment, the repeat units derived from free monomer species B1 and C1 are in a wt % ratio of approximately 3:1.

Figure 4:
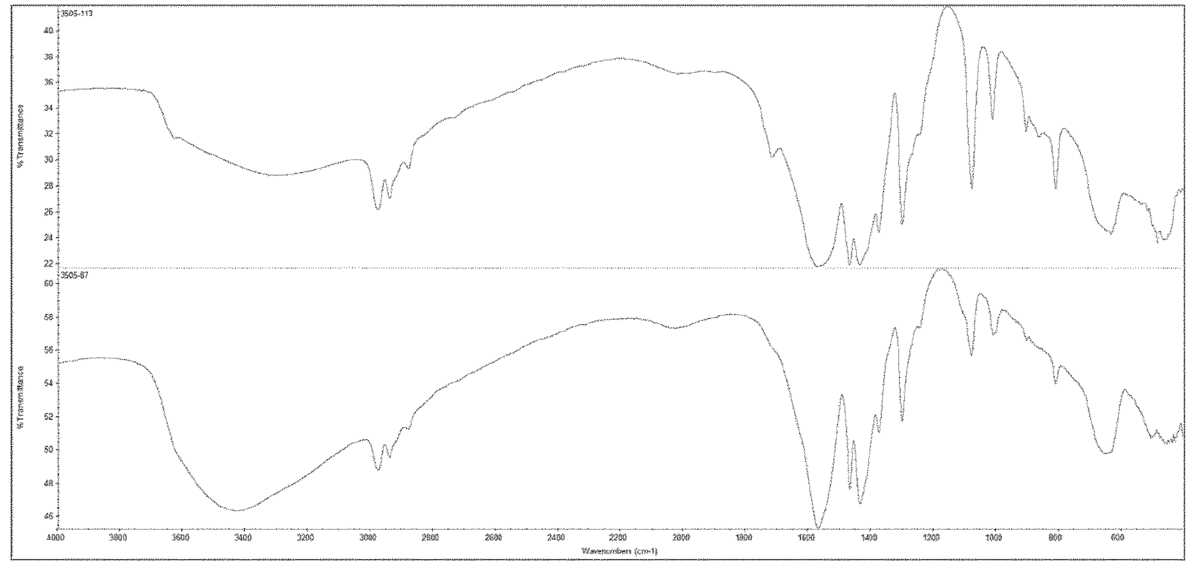
FIG. 4 illustrates the FTIR of ZPP with an —OH absorption band.

The hydroxyl group (which includes (i) bridging hydroxyl groups (i.e., protonated species) and (ii) any —OH groups from monomeric or polymeric species present) to propionate ligand ratio can be approximated by proton NMR. This can be accomplished by comparing the integration values of the —OH peaks and the $—O(C{=}O)CH_2—CH_3$ peaks (attributable to the propionate ligands) in the proton NMR and then adjusting the ratio to account for the amount of water in a given ZPP sample (e.g., by a Karl-Fischer measurement) in view of an elemental analysis of the ZPP material being used. FIG. 4 shows FTIR spectra of ZPP before (shown at bottom) and after (shown at top) thermal treatment (ca. >100° C.). After thermal treatment, there is a decrease in the —OH absorption band around 3400-3600 $cm^{-1}$. This indicates that water, propionic acid and possibly ZrOH, are being removed by this thermal treatment. The water would be removed by evaporation while some ZrOH might be removed by formation of a Zr—O—Zr bridging group and free water. The water formed by any Zr—O—Zr bridging group formation would then also evaporate upon this thermal treatment.

For example, a ZPP sample having an elemental analysis of C: 21.1, H:3.91, Zr:32 most closely aligns with an oligomer or polymeric material that predominantly includes ZPP monomer species B1 (where B1 may be present in free form and as part of the oligomeric or polymeric sample as B2 or B3). Based on this approximation, ZPP monomer species B1 has a calculated elemental analysis of C:26.56, H:4.46, Zr: 33.16 and a Mw of 271.38. If the ZPP sample has a water content of about 4.64 wt %, it would mean that ZPP sample includes at most about 95-96 wt % of the ZPP B1-B3 species. This equates to about 58 mole % of hydroxyl groups (i.e., bridging hydroxyl groups and any —OH groups from monomeric or polymeric species present) and about 42 mole % of water (due to the much larger effect of two —OH groups in the much higher Mw B1-B3 ZPP species compared to a lone —OH in a much lower Mw $H_2O$ molecule). This value then be used to adjust the integration values obtained from a proton NMR using a suitable proton NMR solvent (e.g., $CDCl_3$, pyridine-d5 or THF-d8 with a small amount of $D_2O$) where the solvent does not cutoff the spectrum the —OH peak. A preferred solvent is pyridine-d5 with a small amount of added $D_2O$.

Figure 5:
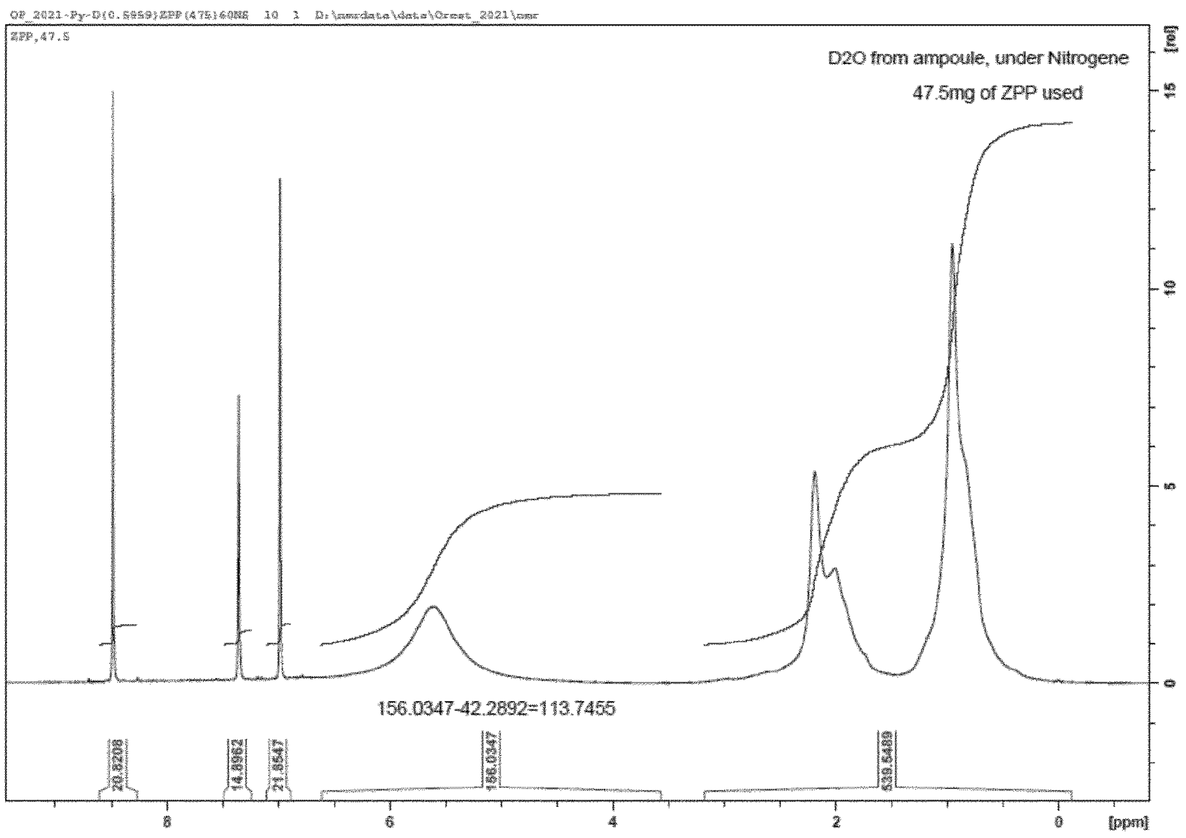
FIG. 5 illustrates an integrated proton NMR of ZPP.
Figure 6:
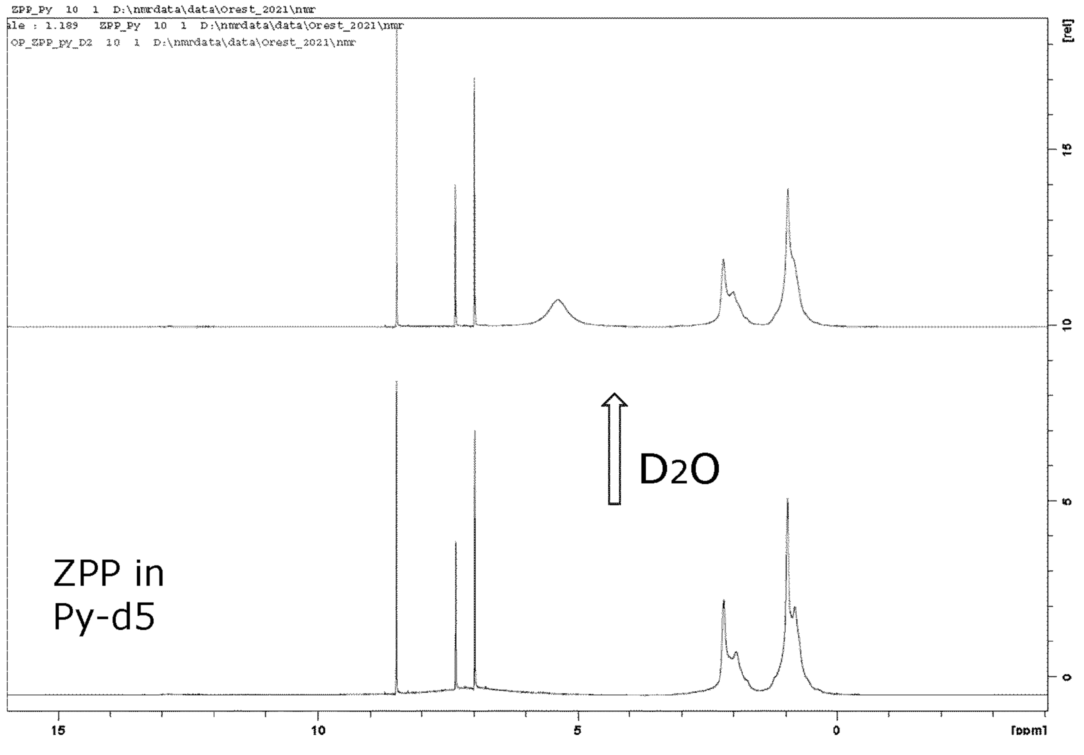
FIG. 6 illustrates the effect on the proton NMR based upon the addition of the $D_2O$.

For example, FIG. 5 shows the proton NMR of ZPP in pyridine-d5 with a small amount of added $D_2O$ (with a blank control correcting for $H_2O$ impurity in the $D_2O$ ca. 42.3 integration intensity) where the —OH peak is between about 5.5 and 6 ppm (integration=156) and the propionate ligand (i.e., $—CH_2CH_3$) peaks at about 0.5 to 2.5 ppm (integration=539.5/5 protons=107.9) are integrated (FIG. 6 compares the effect on the proton NMR based upon the addition of the $D_2O$). The —OH peak is then adjusted to exclude $H_2O$ by multiplying by the estimated mole % of hydroxyl groups (i.e., 113.7×0.58=65.9). This leads to a ratio of —OH to propionate ligands of about 0.61 (i.e., 65.9/107.9=0.61). As those skilled in the art will recognize, the —OH to propionate ligand ratio will have some variability due to the fact that the ZPP samples are oligomeric or polymeric and likely contain more than one of the ZPP species shown in Table 2. As such, this will affect estimating mole percent values for non-$H_2O$ hydroxyl groups and water in a given sample and the derived hydroxyl group to propionate ligand ratio. However, this value enables the ZPP being used in formulations thereof to be better characterized and is useful for adjusting the ZPP in a given formulation as needed in a specific application setting.

Using the forgoing measurement methodology, in one embodiment, the ZPP includes an oligomer or polymeric species having hydroxyl group to propionate ligand ratio of about 0.5 to about 1.1 as measured by proton NMR. In a further aspect of this embodiment, the hydroxyl group to propionate ligand ratio is about 0.55 to about 1.05 as measured by proton NMR. In a further aspect of this embodiment, the hydroxyl group to propionate ligand ratio is about 0.6 to about 0.9 as measured by proton NMR. In a further aspect of this embodiment, the hydroxyl group to propionate ligand ratio is about 0.7 to about 0.8 as measured by proton NMR. In a further aspect of this embodiment, the hydroxyl group to propionate ligand ratio is about 0.5 as measured by proton NMR. In a further aspect of this embodiment, the hydroxyl group to propionate ligand ratio is about 0.55 as measured by proton NMR. In a further aspect of this embodiment, the hydroxyl group to propionate ligand ratio is about 0.6 as measured by proton NMR. In a further aspect of this embodiment, the hydroxyl group to propionate ligand ratio is about 0.65 as measured by proton NMR. In a further aspect of this embodiment, the hydroxyl group to propionate ligand ratio is about 0.7 as measured by proton NMR. In a further aspect of this embodiment, the hydroxyl group to propionate ligand ratio is about 0.75 as measured by proton NMR. In a further aspect of this embodiment, the hydroxyl group to propionate ligand ratio is about 0.8 as measured by proton NMR. In a further aspect of this embodiment, the hydroxyl group to propionate ligand ratio is about 0.85 as measured by proton NMR. In a further aspect of this embodiment, the hydroxyl group to propionate ligand ratio is about 0.9 as measured by proton NMR. In a further aspect of this embodiment, the hydroxyl group to propionate ligand ratio is about 0.55 as measured by proton NMR. In a further aspect of this embodiment, the hydroxyl group to propionate ligand ratio is about 1.0 as measured by proton NMR. In a further aspect of this embodiment, the hydroxyl group to propionate ligand ratio is about 1.05 as measured by proton NMR. In a further aspect of this embodiment, the hydroxyl group to propionate ligand ratio is about 1.1 as measured by proton NMR.

In one embodiment, the ZPP includes zirconium propionate with CAS No. 84057-80-7.

In one embodiment, the ZPP includes between about 0.5 wt % to about 6 wt % of water. In one embodiment, the ZPP includes between about 1 wt % to about 5 wt % of water. In one embodiment, the ZPP includes between about 2 wt % to about 5 wt % of water. In one embodiment, the ZPP includes between about 3 wt % to about 5 wt % of water. In one embodiment, the ZPP includes between about 4 wt % to about 5 wt % of water. In one embodiment, the ZPP includes about 5 wt % of water or less. In one embodiment, the ZPP includes about 4 wt % of water or less. In one embodiment, the ZPP includes about 3 wt % of water or less. In one embodiment, the ZPP includes about 2 wt % of water or less. In one embodiment, the ZPP includes about 1 wt % of water or less.

In one embodiment, the ZPP includes between about 0.5 wt % to about 6 wt %, preferably to about 5 wt % of propionic acid. In one embodiment, the ZPP includes between about 1 wt % to about 5 wt % of propionic acid. In one embodiment, the ZPP includes between about 2 wt % to about 5 wt % of propionic acid. In one embodiment, the ZPP includes between about 3 wt % to about 5 wt % of propionic acid. In one embodiment, the ZPP includes between about 4 wt % to about 5 wt % of propionic acid. In one embodiment, the ZPP includes about 5 wt % of propionic acid or less. In one embodiment, the ZPP includes about 4 wt % of propionic acid or less. In one embodiment, the ZPP includes about 3 wt % of propionic acid or less. In one embodiment, the ZPP includes about 2 wt % of propionic acid or less. In one embodiment, the ZPP includes about 1 wt % of propionic acid or less.

Figure 7:
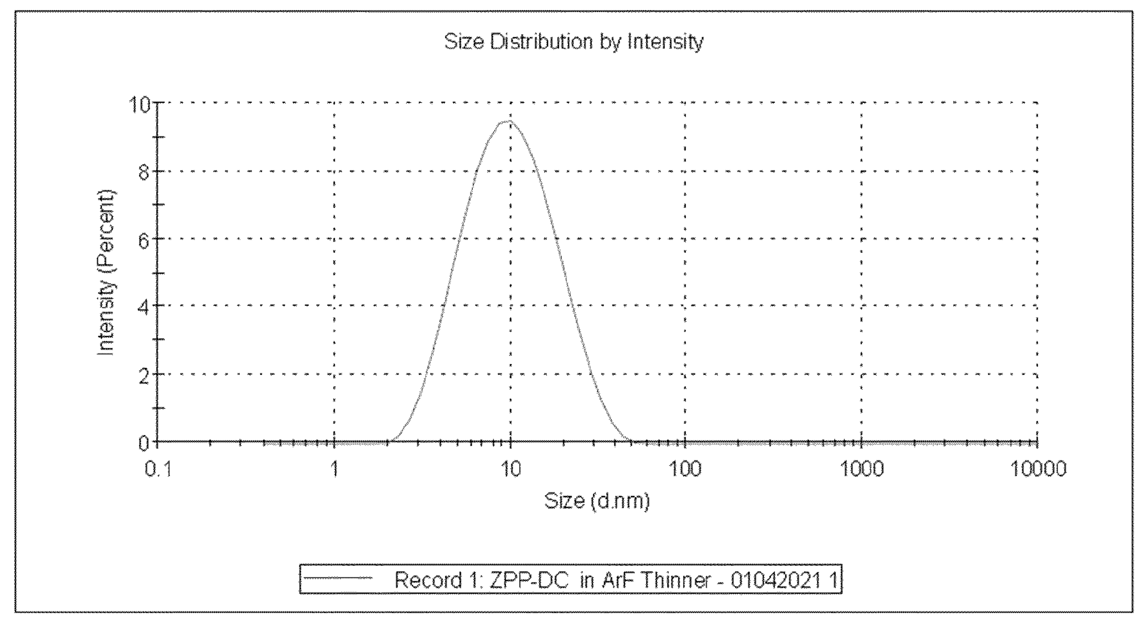
FIG. 7 is a dynamic light scattering (DLS) analysis of ZPP.
Figure 8:
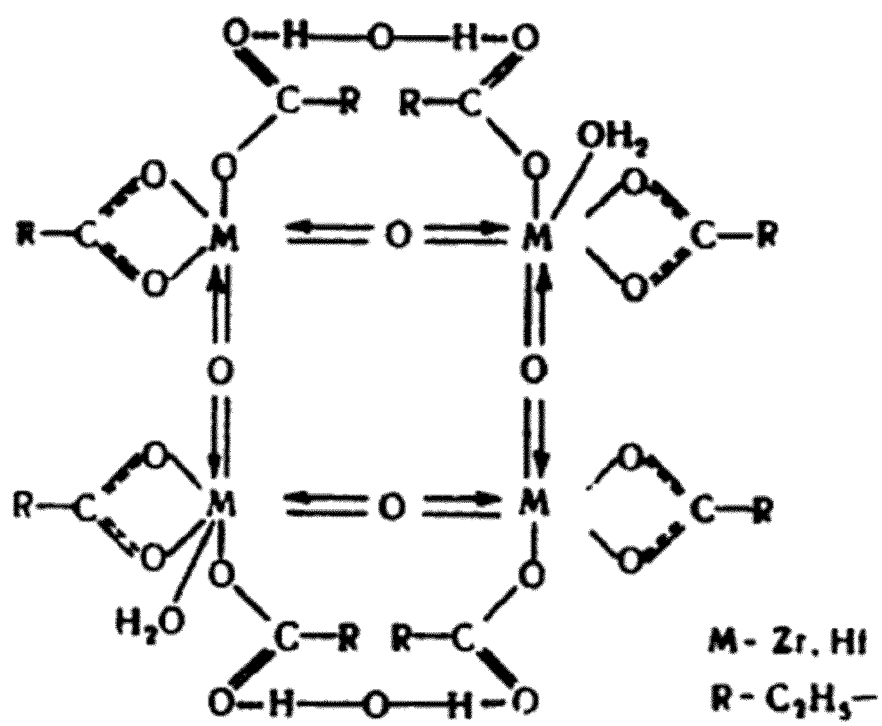
FIGS. 8-10 show structures of zirconium propionates known in the art discussed above.
Figure 9:
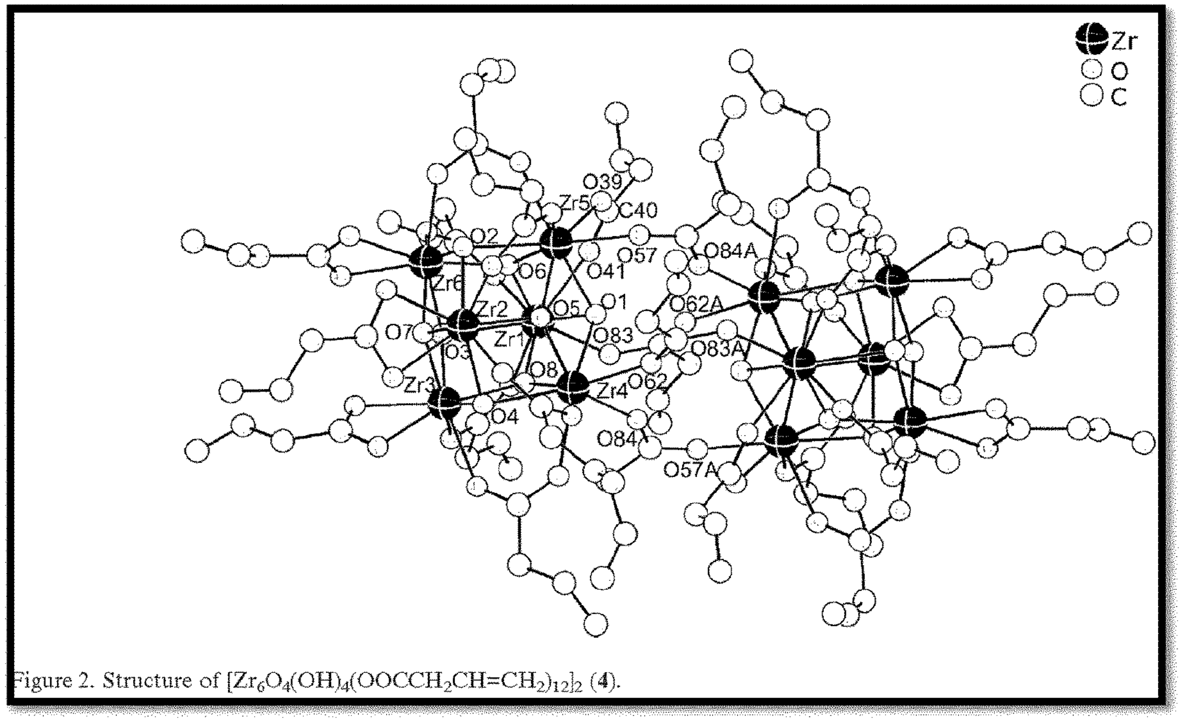
Figure 10:
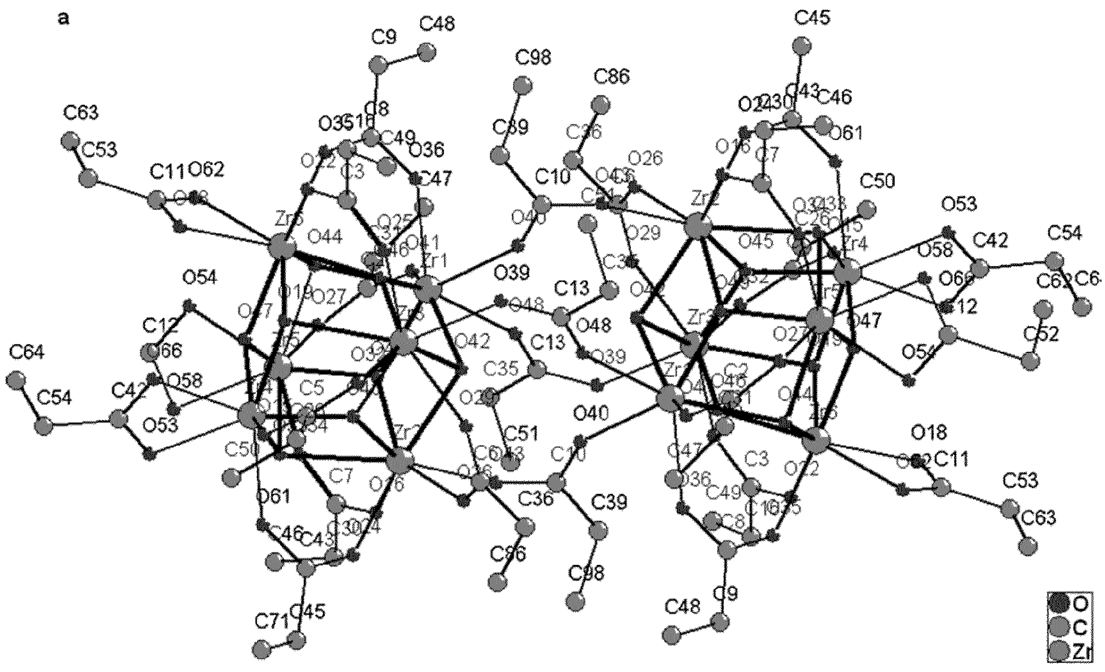

As shown in FIG. 7, the average (i.e., mean) diameter (nm) of ZPP can be measured by dynamic light scattering (DLS). In one embodiment, the ZPP has an average diameter (nm) of about 7.0 nm to about 12.0 nm. In one embodiment, the ZPP has an average diameter (nm) of about 7.5 nm to about 11.5 nm. In one embodiment, the ZPP has an average diameter (nm) of about 8.0 nm to about 11.0 nm. In one embodiment, the ZPP has an average diameter (nm) of about 8.5 nm to about 10.5 nm. In one embodiment, the ZPP has an average diameter (nm) of about 9.0 nm to about 10.0 nm. In one embodiment, the ZPP has an average diameter (nm) of about 7.0 nm. In one embodiment, the ZPP has an average diameter (nm) of about 7.5 nm. In one embodiment, the ZPP has an average diameter (nm) of about 8.0 nm. In one embodiment, the ZPP has an average diameter (nm) of about 8.5 nm. In one embodiment, the ZPP has an average diameter (nm) of about 9.0 nm. In one embodiment, the ZPP has an average diameter (nm) of about 9.5 nm. In one embodiment, the ZPP has an average diameter (nm) of about 10.0 nm. In one embodiment, the ZPP has an average diameter (nm) of about 10.5 nm. In one embodiment, the ZPP has an average diameter (nm) of about 11.0 nm. In one embodiment, the ZPP has an average diameter (nm) of about 11.5 nm. In one embodiment, the ZPP has an average diameter (nm) of about 12.0 nm.

ZPP and ZPPA Formulations

In another aspect, the disclosed and claimed subject matter relates to formulations and the preparation thereof that include ZPP and/or ZPPA.

In one embodiment, the formulations include (i) a zirconium-contain material selected from the group of (a) ZPPA, (b) ZPP) and (c) combinations thereof, (ii) one or more etch resistance modulator additive and (iii) one or more solvents. In a further aspect, the formulations consist essentially of (i) a zirconium-contain material selected from the group of (a) ZPPA, (b) ZPP) and (c) combinations thereof, (ii) one or more etch resistance modulator additive and (iii) one or more solvents. In a further aspect, the formulations consist of (i) a zirconium-contain material selected from the group of (a) ZPPA, (b) ZPP) and (c) combinations thereof, (ii) one or more etch resistance modulator additive and (iii) one or more solvents. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME).

In another embodiment, the formulations above further include one or both of (iv) one or more surfactant and (v) one or more water resistivity enhancer.

Thus, in another embodiment, the formulations include (i) a zirconium-contain material selected from the group of (a) ZPPA, (b) ZPP) and (c) combinations thereof, (ii) one or more etch resistance modulator additive and (iii) one or more solvents and (iv) one or more surfactant. In a further aspect, the formulations consist essentially of (i) a zirconium-contain material selected from the group of (a) ZPPA, (b) ZPP) and (c) combinations thereof, (ii) one or more etch resistance modulator additive and (iii) one or more solvents and (iv) one or more surfactant. In a further aspect, the formulations consist of (i) a zirconium-contain material selected from the group of (a) ZPPA, (b) ZPP) and (c) combinations thereof, (ii) one or more etch resistance modulator additive and (iii) one or more solvents and (iv) one or more surfactant. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred surfactant is an organosiloxane polymer, and in particular an organosiloxane polymer sold under the tradename X-22-4952 (manufactured by Shin-Etsu Chemical Co., Ltd.).

In another embodiment, the formulations include (i) a zirconium-contain material selected from the group of (a) ZPPA, (b) ZPP) and (c) combinations thereof, (ii) one or more etch resistance modulator additive and (iii) one or more solvents and (v) one or more water resistivity enhancer. In a further aspect, the formulations consist essentially of (i) a zirconium-contain material selected from the group of (a) ZPPA, (b) ZPP) and (c) combinations thereof, (ii) one or more etch resistance modulator additive and (iii) one or more solvents and (v) one or more water resistivity enhancer. In a further aspect, the formulations consist of (i) a zirconium-contain material selected from the group of (a) ZPPA, (b) ZPP) and (c) combinations thereof, (ii) one or more etch resistance modulator additive and (iii) one or more solvents and (v) one or more water resistivity enhancer. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred water resistivity enhancer is isobutyric acid.

In yet another embodiment, the formulations include (i) a zirconium-contain material selected from the group of (a) ZPPA, (b) ZPP) and (c) combinations thereof, (ii) one or more etch resistance modulator additive and (iii) one or more solvents, (iv) one or more surfactant and (v) one or more water resistivity enhancer. In a further aspect, the formulations consist essentially of (i) a zirconium-contain material selected from the group of (a) ZPPA, (b) ZPP) and (c) combinations thereof, (ii) one or more etch resistance modulator additive and (iii) one or more solvents, (iv) one or more surfactant and (v) one or more water resistivity enhancer. In a further aspect, the formulations consist of (i) a zirconium-contain material selected from the group of (a) ZPPA, (b) ZPP) and (c) combinations thereof, (ii) one or more etch resistance modulator additive and (iii) one or more solvents, (iv) one or more surfactant and (v) one or more water resistivity enhancer. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred surfactant is X-22-4952. In each of these embodiments, a preferred water resistivity enhancer is isobutyric acid.

In one embodiment, the formulations include (i) ZPPA, (ii) one or more etch resistance modulator additive and (iii) one or more solvents. In a further aspect, the formulations consist essentially of (i) ZPPA, (ii) one or more etch resistance modulator additive and (iii) one or more solvents. In a further aspect, the formulations consist of (i) ZPPA, (ii) one or more etch resistance modulator additive and (iii) one or more solvents. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME).

In another embodiment, the formulations above further include one or both of (iv) one or more surfactant and (v) one or more water resistivity enhancer.

Thus, in another embodiment, the formulations include (i) ZPPA, (ii) one or more etch resistance modulator additive and (iii) one or more solvents and (iv) one or more surfactant. In a further aspect, the formulations consist essentially of (i) ZPPA, (ii) one or more etch resistance modulator additive and (iii) one or more solvents and (iv) one or more surfactant. In a further aspect, the formulations consist of (i) ZPPA, (ii) one or more etch resistance modulator additive and (iii) one or more solvents and (iv) one or more surfactant. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred surfactant is an organosiloxane polymer, and in particular an organosiloxane polymer sold under the tradename X-22-4952 (manufactured by Shin-Etsu Chemical Co., Ltd.).

In another embodiment, the formulations include (i) ZPPA, (ii) one or more etch resistance modulator additive and (iii) one or more solvents and (v) one or more water resistivity enhancer. In a further aspect, the formulations consist essentially of (i) ZPPA, (ii) one or more etch resistance modulator additive and (iii) one or more solvents and (v) one or more water resistivity enhancer. In a further aspect, the formulations consist of (i) ZPPA, (ii) one or more etch resistance modulator additive and (iii) one or more solvents and (v) one or more water resistivity enhancer. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred water resistivity enhancer is isobutyric acid.

In yet another embodiment, the formulations include (i) ZPPA, (ii) one or more etch resistance modulator additive and (iii) one or more solvents, (iv) one or more surfactant and (v) one or more water resistivity enhancer. In a further aspect, the formulations consist essentially of (i) ZPPA, (ii) one or more etch resistance modulator additive and (iii) one or more solvents, (iv) one or more surfactant and (v) one or more water resistivity enhancer. In a further aspect, the formulations consist of (i) ZPPA, (ii) one or more etch resistance modulator additive and (iii) one or more solvents, (iv) one or more surfactant and (v) one or more water resistivity enhancer. In each of these embodiments, a preferred etch resistance modulator additive is 4,4',4"-trihydroxytriphenylmethane ("THTPM"). In each of these embodiments, a preferred solvent is AZ© ArF Thinner (i.e., a mixture of PGMEA and PGME). In each of these embodiments, a preferred surfactant is X-22-4952. In each of these embodiments, a preferred water resistivity enhancer is isobutyric acid.

In one embodiment, the formulations include (i) ZPP, (ii) one or more etch resistance modulator additive and (iii) one or more solvents. In a further aspect, the formulations consist essentially of (i) ZPP, (ii) one or more etch resistance modulator additive and (iii) one or more solvents. In a further aspect, the formulations consist of (i) ZPP, (ii) one or more etch resistance modulator additive and (iii) one or more solvents. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME).

In another embodiment, the formulations above further include one or both of (iv) one or more surfactant and (v) one or more water resistivity enhancer.

Thus, in another embodiment, the formulations include (i) ZPP, (ii) one or more etch resistance modulator additive and (iii) one or more solvents and (iv) one or more surfactant. In a further aspect, the formulations consist essentially of (i) ZPP, (ii) one or more etch resistance modulator additive and (iii) one or more solvents and (iv) one or more surfactant. In a further aspect, the formulations consist of (i) ZPP, (ii) one or more etch resistance modulator additive and (iii) one or more solvents and (iv) one or more surfactant. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred surfactant is X-22-4952.

In another embodiment, the formulations include (i) ZPP, (ii) one or more etch resistance modulator additive and (iii) one or more solvents and (v) one or more water resistivity enhancer. In a further aspect, the formulations consist essentially of (i) ZPP, (ii) one or more etch resistance modulator additive and (iii) one or more solvents and (v) one or more water resistivity enhancer. In a further aspect, the formulations consist of (i) ZPP, (ii) one or more etch resistance modulator additive and (iii) one or more solvents and (v) one or more water resistivity enhancer. In each of these embodiments, a preferred etch resistance modulator additive is 4,4',4"-trihydroxytriphenylmethane ("THTPM"). In each of these embodiments, a preferred solvent is AZ® ArF Thinner (i.e., a mixture of PGMEA and PGME). In each of these embodiments, a preferred water resistivity enhancer is isobutyric acid.

In yet another embodiment, the formulations include (i) ZPP, (ii) one or more etch resistance modulator additive and (iii) one or more solvents, (iv) one or more surfactant and (v) one or more water resistivity enhancer. In a further aspect, the formulations consist essentially of (i) ZPP, (ii) one or more etch resistance modulator additive and (iii) one or more solvents, (iv) one or more surfactant and (v) one or more water resistivity enhancer. In a further aspect, the formulations consist of (i) ZPP, (ii) one or more etch resistance modulator additive and (iii) one or more solvents, (iv) one or more surfactant and (v) one or more water resistivity enhancer. In each of these embodiments, a preferred etch resistance modulator additive is 4,4',4"-trihydroxytriphenylmethane ("THTPM"). In each of these embodiments, a preferred solvent is AZ© ArF Thinner (i.e., a mixture of PGMEA and PGME). In each of these embodiments, a preferred surfactant is X-22-4952. In each of these embodiments, a preferred water resistivity enhancer is isobutyric acid.

(ii) Etch Resistance Modulating Additive

One or more etch resistance modulating additives are added for the purpose of improving the coating formation property of the coating to be formed, preventing intermixing with an upper layer (such as a silicon-containing interlayer and a resist), and/or preventing diffusion of a low-molecular-weight component into the upper layer.

Exemplified embodiments of the etch resistance modulating additives include: melamine, guanamine, glycoluril, and urea compounds substituted by at least one group selected from a methylol group, an alkoxymethyl group, and an acyloxymethyl group; epoxy compounds; thioepoxy compounds; isocyanate compounds; azide compounds; and compounds having a double bond-containing group such as an alkenyl ether group. These may be used as an additive or may alternatively be introduced as a pendant group into a polymer side chain. Preferably, compounds containing a hydroxy group or multiple hydroxy groups can be used as the etch resistance modulating additives.

Examples of the epoxy compounds include tris(2,3-epoxypropyl) isocyanurate, trimethylolmethane triglycidyl ether, trimethylolpropane triglycidyl ether, and triethylolethane triglycidyl ether. Examples of the melamine compounds include hexamethylolmelamine, hexamethoxymethylmelamine, and any mixture of any of such compounds. Examples of the guanamine compounds include tetramethylolguanamine, tetramethoxymethylguanamine, and any mixture of any of such compounds. Examples of the glycoluril compounds include tetramethylolglycoluril, tetramethoxyglycoluril, tetramethoxymethylglycoluril, and any mixture of any of such compounds. Examples of the urea compounds include tetramethylolurea, and tetramethoxymethylurea.

Examples of the compounds containing an alkenyl ether group include ethylene glycol divinyl ether, and triethylene glycol divinyl ether.

Examples of the etch resistance modulating additives containing a hydroxy group or multiple hydroxy groups include those represented by structure (1).

(1)

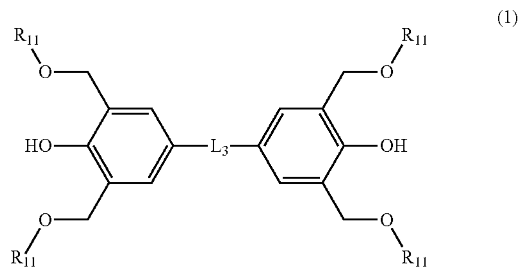

In structure (1), $R_{11}$ is hydrogen or methyl and $L_3$ is a direct bond, substituted or unsubstituted $C_{1-3}$ alkyl, or substituted or unsubstituted $C_{7-16}$ aralkyl. $L_3$ is preferably a direct bond, $C_1$ alkyl, or $C_{15}$ aralkyl. The substituent of the alkyl or aralkyl is preferably hydrogen, methyl, $C_{6-11}$ aryl, or a substituent of structure (1a):

(1a)

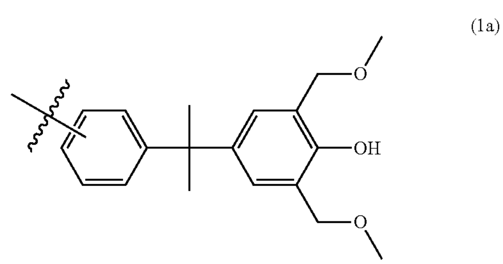

or structure (1b):

(1b)

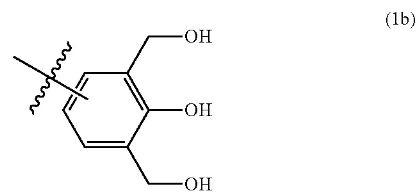

In a preferred aspect, $L_3$ is unsubstituted $C_{1-3}$ alkyl or unsubstituted $C_{1-3}$ aralkyl.

The following are exemplified embodiments of the etch resistance modulating additives represented by structure (1). The disclosed and claimed subject matter is not limited to these examples.

TABLE 3

| Number | Compound |
| --- | --- |
| (1C) | 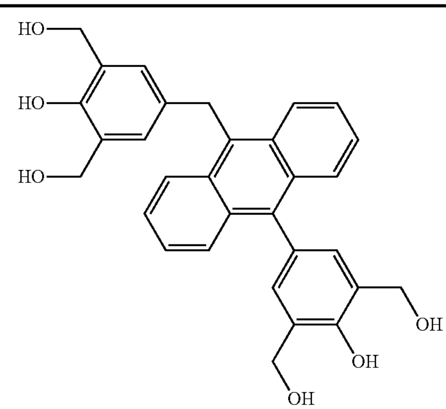 |
| (1D) | 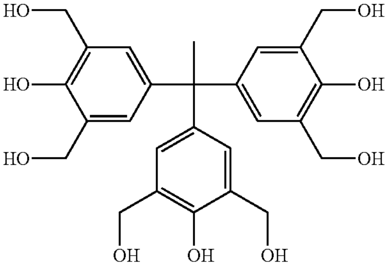 [SMILES: CC(c1cc(CO)c(O)c(CO)c1)(c1cc(CO)c(O)c(CO)c1)c1cc(CO)c(O)c(CO)c1] |

TABLE 3-continued

| Number | Compound |
|---|---|
| (1E) | 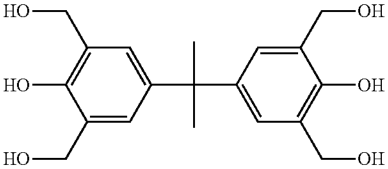 [SMILES: CC(C)(c1cc(CO)c(O)c(CO)c1)c1cc(CO)c(O)c(CO)c1] |
| (1F) | 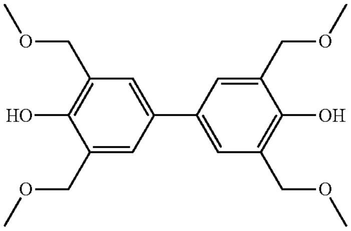 |

TABLE 3-continued

| Number | Compound |
|---|---|
| (1G) | 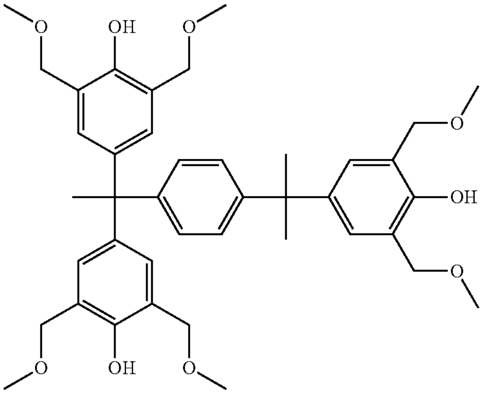 |

Other examples of the etch resistance modulating additives containing a hydroxy group or multiple hydroxy groups include those having monomeric, dimeric (two) or more such as trimeric phenolic compound, tetramer phenol moieties, or higher (e.g., 10 phenolic moieties) where the phenolic moieties in these compounds are linked together through a linking group such as an alkylene moiety, an oxy moiety, a $—SO_2—$ moiety and the like. Non-limiting examples of such compounds are shown in structures (2), (2A), (MB), (3), (3A), (MB), (3C), (3D3) and (4) to (18), wherein the linking groups Xp and Xpa are independently selected from a —O—, $—CH_2—$, $—C(CH_3)_2—$, $—SO_2—$; Rp1 is hydrogen or an alkyl moiety, Rp2, Rp3, Rp4, Rp5 are independently selected from hydrogen or an alkyl moiety.

TABLE 4

| Number | Compound |
|---|---|
| (2) | 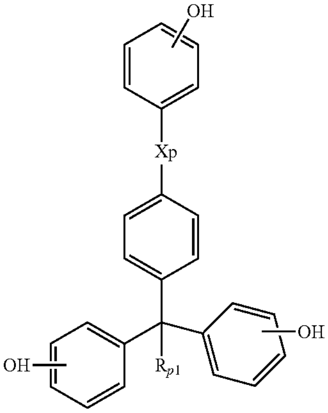 |

TABLE 4-continued
| Number | Compound |
| --- | --- |
| (2A) | 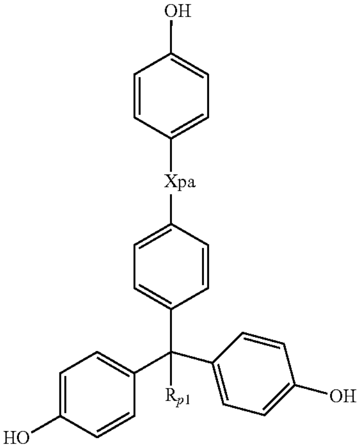 |
| (2B) | 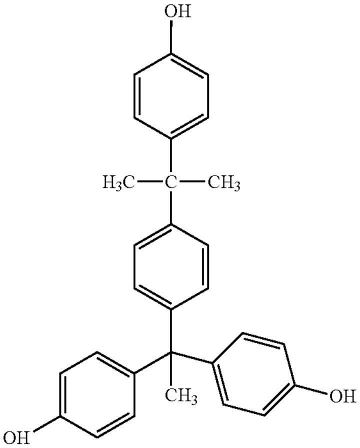 [SMILES: CC(C)(c1ccc(O)cc1)c1ccc(C(C)(c2ccc(O)cc2)c2ccc(O)cc2)cc1] |
| (3) | 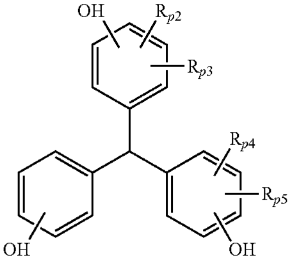 |
| (3A) | 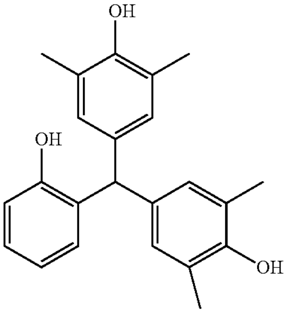 [SMILES: Cc1cc(C(c2cc(C)c(O)c(C)c2)c2ccccc2O)cc(C)c1O] |

TABLE 4-continued
| Number | Compound |
| --- | --- |
| (3B) | 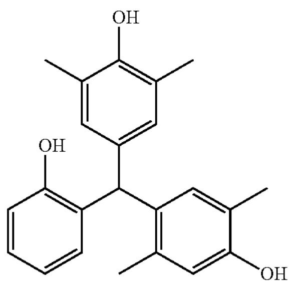 [SMILES: Cc1cc(C(c2cc(C)c(O)c(C)c2)c2ccccc2O)c(C)cc1O] |
| (3C) | 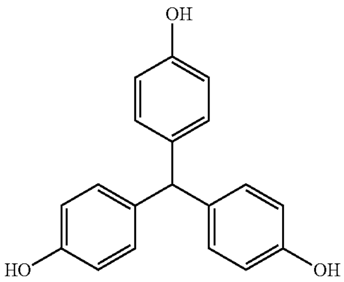 [SMILES: Oc1ccc(C(c2ccc(O)cc2)c2ccc(O)cc2)cc1] |
| (3D) | 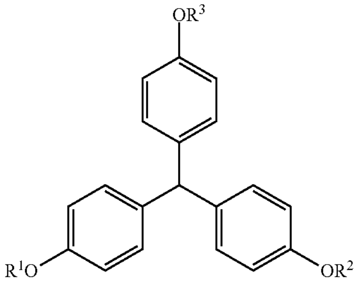<br>where $R^1$ and $R^2$ are each independently H, $—C(═O)C_2H_5$, $—C(═O)C_3H_7$, or $—C(═O)C_4H_9$; and where $R^3$ is independently $—C(═O)C_2H_5$, $—C(═O)C_3H_7$, or $—C(═O)C_4H_9$. |
| (4) | 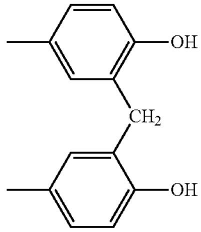 [SMILES: Cc1ccc(O)c(Cc2cc(C)ccc2O)c1] |
| (5) | 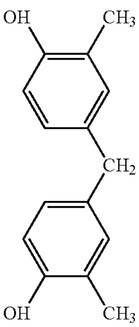 [SMILES: Cc1cc(Cc2ccc(O)c(C)c2)ccc1O] |

TABLE 4-continued
| Number | Compound |
|---|---|
| (6) | 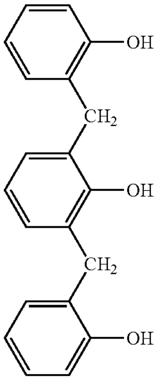 [SMILES: Oc1ccccc1Cc1cccc(Cc2ccccc2O)c1O] |
| | (7) |
| (8) | 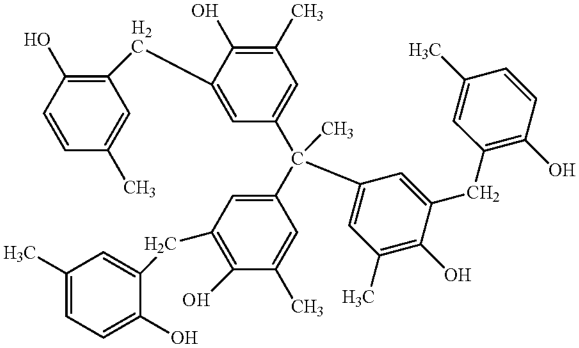 [SMILES: Cc1ccc(O)c(Cc2cc(C(C)(c3cc(C)c(O)c(Cc4cc(C)ccc4O)c3)c3cc(C)c(O)c(Cc4cc(C)ccc4O)c3)cc(C)c2O)c1] |
| (9) | 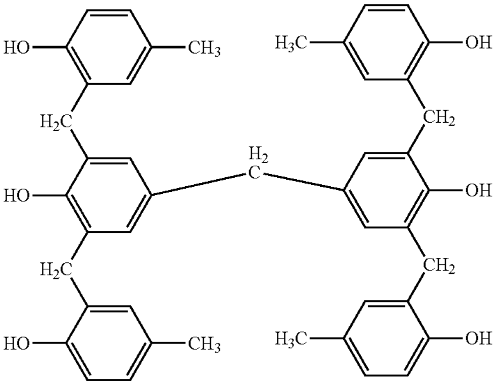 [SMILES: Cc1ccc(O)c(Cc2cc(Cc3cc(Cc4cc(C)ccc4O)c(O)c(Cc4cc(C)ccc4O)c3)cc(Cc3cc(C)ccc3O)c2O)c1] |
| (10) | 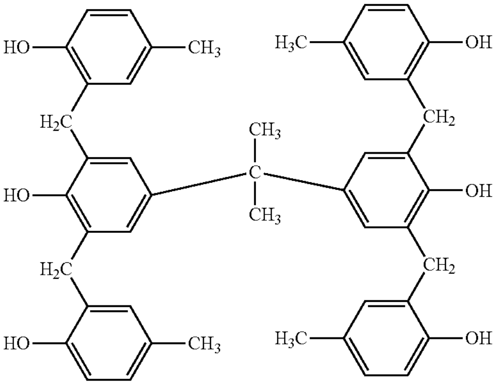 [SMILES: Cc1ccc(O)c(Cc2cc(C(C)(C)c3cc(Cc4cc(C)ccc4O)c(O)c(Cc4cc(C)ccc4O)c3)cc(Cc3cc(C)ccc3O)c2O)c1] |

TABLE 4-continued
| Number | Compound |
|---|---|
| (11) | 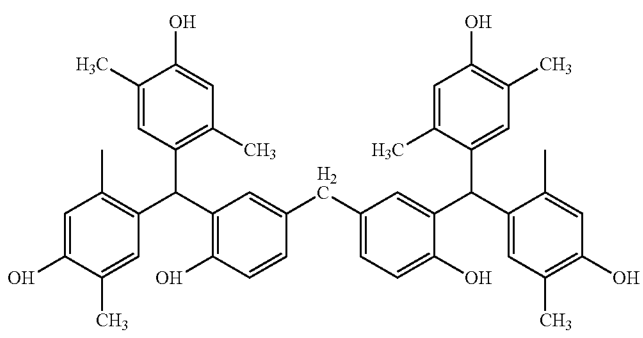 [SMILES: Cc1cc(C(c2cc(C)c(O)cc2C)c2cc(Cc3ccc(O)c(C(c4cc(C)c(O)cc4C)c4cc(C)c(O)cc4C)c3)ccc2O)c(C)cc1O] |
| (12) | 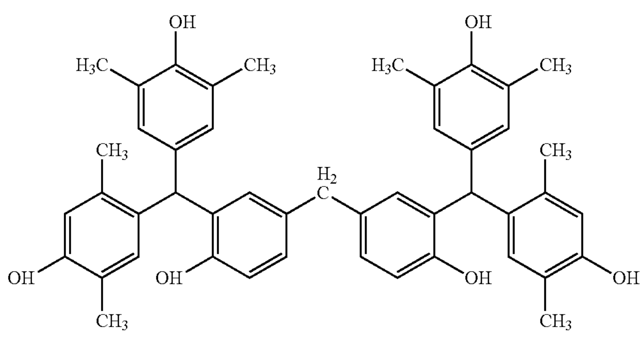 [SMILES: Cc1cc(C(c2cc(C)c(O)c(C)c2)c2cc(Cc3ccc(O)c(C(c4cc(C)c(O)c(C)c4)c4cc(C)c(O)cc4C)c3)ccc2O)c(C)cc1O] |
| (13) | 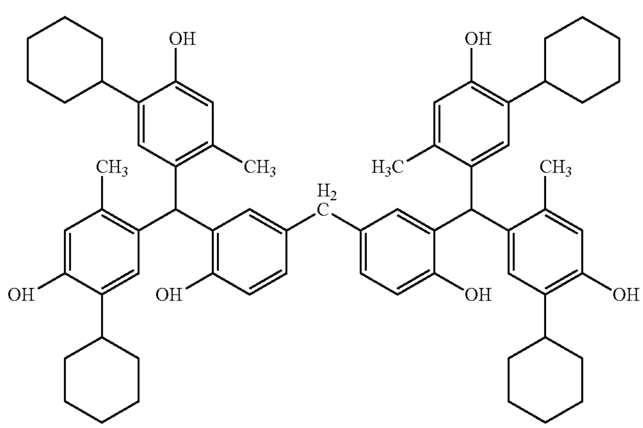 [SMILES: Cc1cc(O)c(C2CCCCC2)cc1C(c1cc(C2CCCCC2)c(O)cc1C)c1cc(Cc2ccc(O)c(C(c3cc(C4CCCCC4)c(O)cc3C)c3cc(C4CCCCC4)c(O)cc3C)c2)ccc1O] |
| (14) | 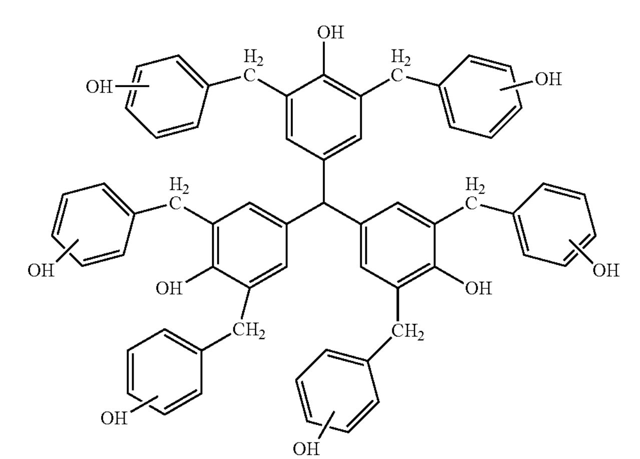 |

TABLE 4-continued
| Number | Compound |
|---|---|
| (15) (NF0327) | 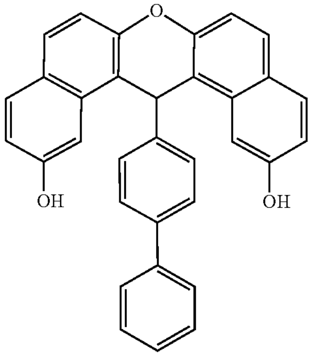 [SMILES: Oc1ccc2ccc3c(c2c1)C(c1ccc(-c2ccccc2)cc1)c1c(ccc2ccc(O)cc12)O3] |
| (16) (NF0A28) | 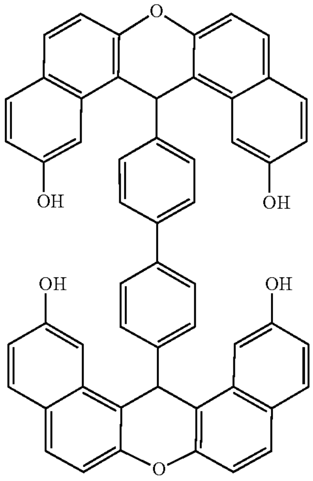 [SMILES: Oc1ccc2ccc3c(c2c1)C(c1ccc(-c2ccc(C4c5c(ccc6ccc(O)cc56)Oc5ccc6ccc(O)cc6c54)cc2)cc1)c1c(ccc2ccc(O)cc12)O3] |
| (17) (NF71A7 | 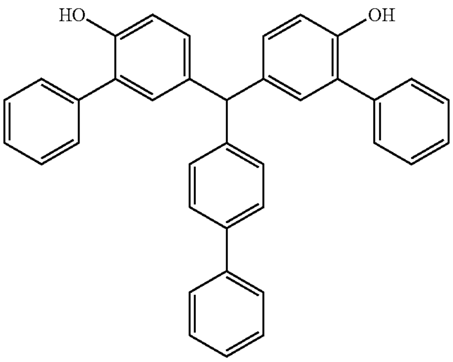 [SMILES: Oc1ccc(C(c2ccc(-c3ccccc3)cc2)c2ccc(O)c(-c3ccccc3)c2)cc1-c1ccccc1] |
| (18) (NF0127) | 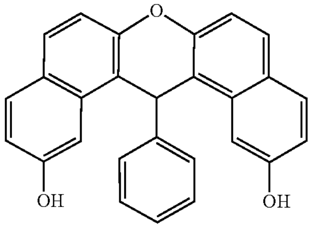 [SMILES: Oc1ccc2ccc3c(c2c1)C(c1ccccc1)c1c(ccc2ccc(O)cc12)O3] |

TABLE 4-continued

| Number | Compound |
|---|---|
| | 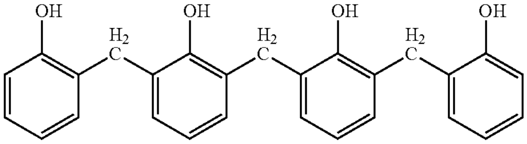 [SMILES: Oc1ccccc1Cc1cccc(Cc2cccc(Cc3ccccc3O)c2O)c1O] |

In one embodiment, the etch resistance modulating additive has structure (3), as described above. In a further aspect of this embodiment, the etch resistance modulating additives has structure (3C) as described above (i.e., 4,4',4"-trihydroxytriphenylmethane; THTPM).

In a further aspect of this embodiment, the etch resistance modulating additives has structure (3D) as described above. In one aspect of this embodiment, each of $R^1$ and $R^2$ is a propionyl group (i.e., 4,4',4"-tripropionyloxytriphenylmethane (THTPM-TP; 3D1)):

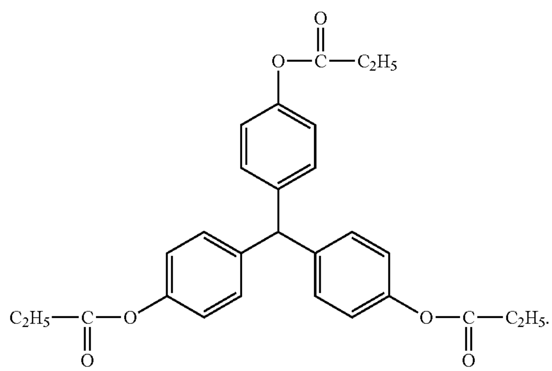 [SMILES: CCC(=O)Oc1ccc(C(c2ccc(OC(=O)CC)cc2)c2ccc(OC(=O)CC)cc2)cc1]

In another aspect of this embodiment, one of $R^1$ and $R^2$ is a propionyl group and the other of $R^1$ and $R^2$ is hydrogen (i.e., $3D_2$):

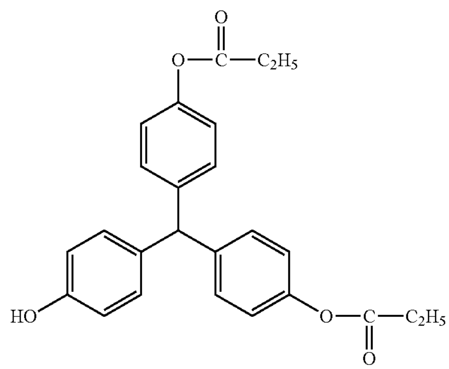 [SMILES: CCC(=O)Oc1ccc(C(c2ccc(O)cc2)c2ccc(OC(=O)CC)cc2)cc1]

In another aspect of this embodiment, each of $R^1$ and $R^2$ is hydrogen (i.e., $3D_3$).

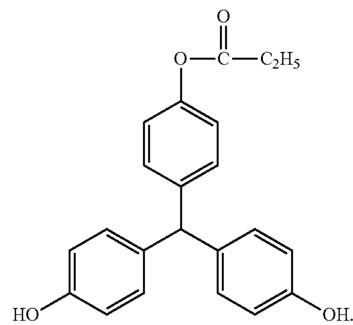 [SMILES: CCC(=O)Oc1ccc(C(c2ccc(O)cc2)c2ccc(O)cc2)cc1]

In a further embodiment, the etch resistance modulating additive is a mixture of more than one etch resistance modulating additive. In one aspect of this embodiment, the mixture includes the etch resistance modulating additives having structure (3C) (i.e., 4,4',4"-trihydroxytriphenylmethane; THTPM). In one aspect of this embodiment, the mixture includes the etch resistance modulating additive having structure ($3D_1$) (i.e., 4,4',4"-tripropionyloxytriphenylmethane (THTPM-TP)). In one aspect of this embodiment, the mixture includes the etch resistance modulating additive having structure (3C) (i.e., 4,4',4"-trihydroxytriphenylmethane; THTPM) and (3D1) (i.e., 4,4',4"-tripropionyloxytriphenylmethane (THTPM-TP)). In another aspect of this embodiment, the mixture includes the etch resistance modulating additives having structure (3C) (i.e., 4,4',4"-trihydroxytriphenylmethane; THTPM) and one or more of the etch resistance modulating additives $3D_1$ (THTPM-TP), $3D_2$ and $3D_3$.

Other polyphenol compounds or polymers can be used as well. Examples of suitable Polyphenol compounds or polymers include those disclosed in U.S. Pat. No. 9,274,426 and/or U.S. Patent Application Publication No. 2012/0251956. Phenolic OH groups can be protected by acid labile groups, such as ester groups, acetal group, also heterocyclic structure can be included in the structures.

Other etch resistance modulating additives are also contemplated. In some embodiments, etch resistance modulating additives (19) or (20) can be included. These crosslinking agents are available, for example, from Sanwa Chemical Co., Ltd., Honshu Chemical Industry Co., Ltd., Asahi Yukizai Corporation, and Nippon Carbide Industries Co., Inc.

TABLE 5

| Number | Compound |
| --- | --- |
| (19) | 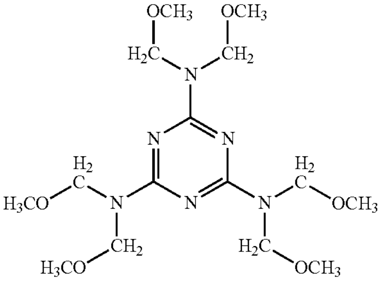 [SMILES: COCN(COC)c1nc(N(COC)COC)nc(N(COC)COC)n1] |
| (20) | 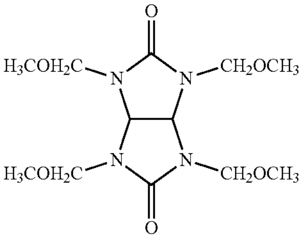 |

In one embodiment of the disclosed and claimed subject matter, the amount of the etch resistance modulating additives is preferably approximately 0.1 wt % to approximately 30 wt % of total solid components in composition. In a further aspect of this embodiment, the amount of the etch resistance modulating additives is approximately 1 wt % to approximately 20 wt %. In a further aspect of this embodiment, the amount of the etch resistance modulating additives is approximately 2 wt % to approximately 15 wt %. In a further aspect of this embodiment, the amount of the etch resistance modulating additives is approximately 5 wt % to approximately 12 wt %. In one embodiment of the disclosed and claimed subject matter, the amount of the etch resistance modulating additives is preferably approximately 0.1 wt % to approximately 1 wt % of total solid components in composition. In one embodiment of the disclosed and claimed subject matter, the amount of the etch resistance modulating additives is preferably approximately 0.5 wt % to approximately 1 wt % of total solid components in composition. In one embodiment of the disclosed and claimed subject matter, the amount of the etch resistance modulating additives is preferably approximately 0.5 wt % to approximately 0.75 wt % of total solid components in composition. In a further aspect of this embodiment, the amount of the etch resistance modulating additives is approximately 0.5 wt %. In a further aspect of this embodiment, the amount of the etch resistance modulating additives is approximately 0.6 wt %. In a further aspect of this embodiment, the amount of the etch resistance modulating additives is approximately 0.7 wt %. In a further aspect of this embodiment, the amount of the etch resistance modulating additives is approximately 0.8 wt %. In a further aspect of this embodiment, the amount of the etch resistance modulating additives is approximately 0.9 wt %. In a further aspect of this embodiment, the amount of the etch resistance modulating additives is approximately 1 wt %. In a further aspect of this embodiment, the amount of the etch resistance modulating additives is approximately 2 wt %. In a further aspect of this embodiment, the amount of the etch resistance modulating additives is approximately 3 wt %. In a further aspect of this embodiment, the amount of the etch resistance modulating additives is approximately 4 wt %. In a further aspect of this embodiment, the amount of the etch resistance modulating additives is approximately 5 wt %. In a further aspect of this embodiment, the amount of the etch resistance modulating additives is approximately 6 wt %. In a further aspect of this embodiment, the amount of the etch resistance modulating additives is approximately 7 wt %. In a further aspect of this embodiment, the amount of the etch resistance modulating additives is approximately 8 wt %. In a further aspect of this embodiment, the amount of the etch resistance modulating additives is approximately 9 wt %. In a further aspect of this embodiment, the amount of the etch resistance modulating additives is approximately 10 wt %.

In one embodiment, the formulation includes about 0.5 wt % to about 5 wt % of 4,4',4"-trihydroxytriphenylmethane (THTPM). In a further aspect of this embodiment, the formulation includes about 2 wt % to about 5 wt % of 4,4',4"-trihydroxytriphenylmethane (THTPM). In a further aspect of this embodiment, the formulation includes about 0.5 wt % to about 0.75 wt % of 4,4',4"-trihydroxytriphenylmethane (THTPM). In a further aspect of this embodiment, the formulation includes about 0.5 wt % to about 1 wt % of 4,4',4"-trihydroxytriphenylmethane (THTPM). In a further aspect of this embodiment, the formulation includes about 1 wt % to about 2 wt % of 4,4',4"-trihydroxytriphenylmethane (THTPM). In a further aspect of this embodiment, the formulation includes about 3 wt % to about 4 wt % of 4,4',4"-trihydroxytriphenylmethane (THTPM).

In a further aspect of this embodiment, the formulation includes about 0.5 wt % of 4,4',4"-trihydroxytriphenylmethane (THTPM). In a further aspect of this embodiment, the formulation includes about 0.6 wt % of 4,4',4"-trihydroxytriphenylmethane (THTPM). In a further aspect of this embodiment, the formulation includes about 0.7 wt % of 4,4',4"-trihydroxytriphenylmethane (THTPM). In a further aspect of this embodiment, the formulation includes about 0.8 wt % of 4,4',4"-trihydroxytriphenylmethane (THTPM). In a further aspect of this embodiment, the formulation includes about 0.9 wt % of 4,4',4"-trihydroxytriphenylmethane (THTPM). In a further aspect of this embodiment, the formulation includes about 1 wt % of 4,4',4"-trihydroxytriphenylmethane (THTPM).

In one embodiment, the formulation includes about 0.5 wt % to about 5 wt % of 4,4',4"-tripropionyloxytriphenylmethane (THTPM-TP). In a further aspect of this embodiment, the formulation includes about 2 wt % to about 5 wt % of 4,4',4"-tripropionyloxytriphenylmethane (THTPM-TP). In a further aspect of this embodiment, the formulation includes about 0.5 wt % to about 0.75 wt % of 4,4',4"-tripropionyloxytriphenylmethane (THTPM-TP). In a further aspect of this embodiment, the formulation includes about 0.5 wt % to about 1 wt % of 4,4',4"-tripropionyloxytriphenylmethane (THTPM-TP). In a further aspect of this embodiment, the formulation includes about 0.5 wt % to about 1 wt % of 4,4',4"-tripropionyloxytriphenylmethane (THTPM-TP). In a further aspect of this embodiment, the formulation includes about 1 wt % to about 2 wt % of 4,4',4"-tripropionyloxytriphenylmethane (THTPM-TP). In a further aspect of this embodiment, the formulation includes about 3 wt % to about 4 wt % of 4,4',4"-tripropionyloxytriphenylmethane (THTPM-TP). In a further aspect of this embodiment, the formulation includes about 0.5 wt % of 4,4',4"-tripropionyloxytriphenylmethane (THTPM-TP). In a further aspect of this embodiment, the formulation includes about 0.6 wt % of 4,4',4"-tripropionyloxytriphenylmethane (THTPM-TP). In a further aspect of this embodiment, the formulation includes about 0.7 wt % of 4,4',4"-tripropionyloxytriphenylmethane (THTPM-TP). In a further aspect of this embodiment, the formulation includes about 0.8 wt % of 4,4',4"-tripropionyloxytriphenylmethane (THTPM-TP). In a further aspect of this embodiment, the formulation includes about 0.9 wt % of 4,4',4"-tripropionyloxytriphenylmethane (THTPM-TP). In a further aspect of this embodiment, the formulation includes about 1 wt % of 4,4',4"-tripropionyloxytriphenylmethane (THTPM-TP).

In one embodiment, the formulation includes about 0.5 wt % to about 0.75 wt % of either of NF0327, NF0A28, NF71A7 or NF0127, as shown in table 4 above. In a further aspect of this embodiment, the formulation includes about 0.6 wt % of either of NF0327, NF0A28, NF71A7 or NF0127, as shown in table 4 above.

In some embodiment, the formulations include more than one etch resistance modulating additive.

(iii) Solvent(s)

As noted above, the ZPP and/or ZPPA formulations include one or more solvents suitable for use in spin casting. In this regard, the one or more solvents can include a glycol ether derivative, a glycol ether ester derivative a carboxylate, a carboxylate of a di-basic acid, a dicarboxylate of a glycol, a hydroxy carboxylate, a ketone ester, an alkyloxy carboxylic acid ester, a ketone derivative, a ketone ether derivative, a ketone alcohol derivative, an amide derivative and mixtures thereof.

In some embodiments, the one or more solvents is a glycolic solvents chosen from alkylene diols, oligo(alkylenoxy) alkylene) diols [HO-(alkylene-O-alkylene-O)$_n$—H] (n=1 to 4), monoalkyl dialkyl ethers, and alkyl carboxylates/alkyl ethers derivatives of alkylene diol monoalkyl and also to mixtures of at least two of these solvents. In a more specific embodiment, the one or more solvent includes an alkylene diol. In another more specific embodiment, the one or more solvent includes an oligo(alkylenoxy) alkylene) diol [HO-(alkylene-O-alkylene-O)n-H](n=1 to 4). In another more specific embodiment, the one or more solvent includes a monoalkyl carboxylates of an alkylene diol. In yet another more specific embodiment, the one or more solvent includes a monoalkyl carboxylate of oligo(alkylenoxy) alkylene) diol [HO-(alkylene-O-alkylene-O)n-H](n=1 to 4). In a more specific embodiment of this aspect, the alkylene moieties in these glycolic derivatives may be a C-2 to C-6 linear alkylene, or a C-3 to C-7 branched alkylene or in the case of the oligo oligo(alkylenoxy) alkylene) a mixture of these. In a more specific embodiment, the alkyl moieties in the monoalkyl ethers, dialkyl ether these are individually selected from methyl, ethyl, propyl, isopropyl, butyl, tert-butyl, isobutyl. In a more specific embodiment, these glycolic solvents containing alkyl carboxylate these alkyl carboxylates are selected from acetate, propionate, isobutyrate, and butyrate. In a more specific embodiment, the glycolic derivative solvent is selected from ethylene glycol, propylene glycol, propylene glycol monomethyl ether acetate (PGMEA), propyleneglycol monomethyl ether (PGME), and di(propylene glycol) methyl ether (DPGME) or a mixture of at least two of these solvents. In a more specific embodiment, the glycolic derivative solvent is selected from propylene glycol, propylene glycol monomethyl ether acetate (PGMEA), propyleneglycol monomethyl ether (PGME) and di(propylene glycol) methyl ether (DPGME) or a mixture of at least two of these solvents.

The term "dipropylene glycol" also designated by dipropylene glycol dimethyl ether or with the abbreviation DPGDME is a mixture with the general formula $CH_3OC_3H_6OC_3H_6OCH_3$. This mixture also has the synonymous name bis(methoxypropyl) ether, DMFG, Proglyde™, DMM and Proglyme™

In some embodiments, the formulations preferably include one or both of PGMEA (propylene glycol monomethyl ether acetate) and PGME (propyleneglycol monomethyl ether). One preferred solvent is AZ® ArF thinner. AZ® ArF thinner is a trivial name for a mixture of 70 wt % of PGMEA and 30 wt % of PGME. Another preferred solvent is AZ® EBR7030 which is a mixture of 30 wt % of PGMEA and 70 wt % of PGME. Other weight ratio mixtures of PGMEA and PGME can also be used such as a mixture of 60 wt % of PGMEA and 40 wt % of PGME etc., or 100% PGMEA.

In one embodiment, the formulations include from about 70 wt % to about 98 wt % of the one or more solvents. In a further aspect of this embodiment, the formulations include from about 70 wt % to about 80 wt % of the one or more solvents. In a further aspect of this embodiment, the formulations include from about 80 wt % to about 90 wt % of the one or more solvents. In a further aspect of this embodiment, the formulations include from about 90 wt % to about 95 wt % of the one or more solvents. In a further aspect of this embodiment, the formulations include from about 90 wt % to about 98 wt % of the one or more solvents. In a further aspect of this embodiment, the formulations include about 90 wt % of the one or more solvents. In a further aspect of this embodiment, the formulations include about 91 wt % of the one or more solvents. In a further aspect of this embodiment, the formulations include about 92 wt % of the one or more solvents. In a further aspect of this embodiment, the formulations include about 93 wt % of the one or more solvents. In a further aspect of this embodiment, the formulations include about 94 wt % of the one or more solvents. In a further aspect of this embodiment, the formulations include about 95 wt % of the one or more solvents. In a further aspect of this embodiment, the formulations include about 96 wt % of the one or more solvents. In a further aspect of this embodiment, the formulations include about 97 wt % of the one or more solvents. In a further aspect of this embodiment, the formulations include about 98 wt % of the one or more solvents.

In one embodiment, the formulation includes about 93 wt % of AZ® ArF Thinner.

In one embodiment, the formulation includes about 94 wt % of AZ® ArF Thinner.

In one embodiment, the formulation includes about 95 wt % of AZ® ArF Thinner.

In one embodiment, the formulation includes about 93 wt % of PGMEA.

In one embodiment, the formulation includes about 94 wt % of PGMEA.

In one embodiment, the formulation includes about 95 wt % of PGMEA.

(iv) Surfactant(s)

As noted above, in some embodiments of ZPP and/or ZPPA formulations can optionally include one or more surfactants. In some embodiments, the amount of the surfactant is from about 0.001 wt % to about 5 wt % of the composition, preferably from about 0.01 wt % to about 2.5 wt % and, more preferably, from about 0.1 wt % to about 1.0 wt % of the composition. In some embodiments, the ZPP and/or ZPPA formulations can include about 1.0 wt % or less of a surfactant.

There is no particular restriction with regard to the surfactant, and the examples of it include a polyoxyethylene alkyl ether such as polyoxyethylene lauryl ether, polyoxyethylene stearyl ether, polyoxyethylene cetyl ether, and polyoxyethylene olein ether; a polyoxyethylene alkylaryl ether such as polyoxyethylene octylphenol ether and polyoxyethylene nonylphenol ether; a polyoxyethylene polyoxypropylene block copolymer; a sorbitane fatty acid ester such as sorbitane monolaurate, sorbitane monovalmitate, and sorbitane monostearate; a nonionic surfactant of a polyoxyethylene sorbitane fatty acid ester such as polyoxyethylene sorbitane monolaurate, polyoxyethylene sorbitane monopalmitate, polyoxyethylene sorbitane monostearate, polyethylene sorbitane trioleate, and polyoxyethylene sorbitane tristearate; a fluorinated surfactant such as Brij 30, Brij 32 (Croda, USA), Triton X-100 (Trion Chemical, USA), F-Top EF301, EF303, and EF352 (Jemco Inc. Japan), Megaface F171, F172, F173, R08, R30, R90, and R94 (DIC Corp, Japan), Florad FC-430, FC-431, FC-4430, and FC-4432 (3M, USA), Asahi Guard AG710, Surflon S-381, S-382, S-386, SC101, SC102, SC103, SC104, SC105, SC106, Surfinol E1004, KH-10, KH-20, KH-30, and KH-40 (Asahi Glass Co., Ltd. Japan); an organosiloxane polymer or a silicone-containing surfactant such as KF53, KP-341, KP-351, X22-4952, X70-092, and X70-093 (ShinEtsu Silicone Co. Ltd., Japan); and an acrylic acid or a methacrylic acid polymer such as Polyflow No. 75 and No. 95 (Kyoeisha Yushikagaku Kogyo K. K. Japan).

In some embodiments, the ZPP and/or ZPPA formulations include one or more silicon containing surfactants. In one aspect of these embodiments, a preferred surfactant is an organosiloxane polymer, and in particular an organosiloxane polymer sold under the tradename X-22-4952.

In one embodiment, the formulation includes about 0.1 wt % to about 0.2 wt % of X-22-4952.

In one embodiment, the formulation includes about 0.1 wt % to about 0.15 wt % of X-22-4952.

In one embodiment, the formulation includes about 0.1 wt % of X-22-4952.

In one embodiment, the formulation includes about 0.15 wt % of X-22-4952.

In one embodiment, the formulation includes about 0.025 wt % to about 0.2 wt % of KF53.

In one embodiment, the formulation includes about 0.025 wt % to about 0.1 wt % of KF53.

In one embodiment, the formulation includes about 0.1 wt % of KF53.

In one embodiment, the formulation includes about 0.05 wt % of KF53.

In one embodiment, the formulation includes about 0.025 wt % of KF53.

In one embodiment, the formulation includes about 0.1 wt % to about 0.5 wt % of KF353A.

In one embodiment, the formulation includes about 0.1 wt % of KF353A.

In one embodiment, the formulation includes about 0.13 wt % of KF353A.

In one embodiment, the formulation includes about 0.2 wt % of KF353A.

In one embodiment, the formulation includes about 0.3 wt % of KF353A.

In one embodiment, the formulation includes about 0.001 wt % to about 0.1 wt % of KP341.

In one embodiment, the formulation includes about 0.001 wt % of KP341.

In one embodiment, the formulation includes about 0.05 wt % of KP341.

In one embodiment, the formulation includes about 0.1 wt % of KP341.

In some embodiments, the compositions of the disclosed and claimed subject matter will be free of or substantially free of surfactants.

(v) Water Resistivity Enhancer

As noted above, the ZPP and/or ZPPA formulations optionally include one or more water resistivity enhancers to affect or improve resistance to moisture.

In one embodiment, the one or more water resistivity enhancers includes one or more alkyl mono-carboxylic acids with 3 to 20 carbons, where the alkyl group may be a linear alkyl, a branched alkyl or a cyclic alkyl. In a further aspect of this embodiment the one or more alkyl mono-carboxylic acid has from 3 to 10 carbon atoms.

In another embodiment, the one or more water resistivity enhancers includes one or more of carboxylic acids, such as propionic acid (PA), n-butyric acid, isobutyric acid (IBA), pentanoic acid, 2-methylbutanoic acid, 3-methylbutanoic acid, tert-butylacetic acid, hexanoic acid, 2-methylpentanoic acid, 3-methylpentanoic acid, 4-methylpentanoic acid, heptanoic acid, 2-methylhexanoic acid, 3-methylhexanoic acid, 4-methylhexanoic acid, 5-methylhexanoic acid, 2,2-dimethylpentanoic acid, 2,3-dimethylpentanoic acid, 2,4-dimethylpentanoic acid, 3,3-dimethylpentanoic acid, 4,4-dimethylpentanoic acid, octanoic acid, 2-methylheptanoic acid, 3-methylheptanoic acid, 4-methylheptanoic acid, 5-methylheptanoic acid, 6-methylheptanoic acid, 2,2-dimethylhexanoic acid, 2,3-dimethylhexanoic acid, 2,4-dimethylhexanoic acid, 2,5-dimethylhexanoic acid, 3,3-dimethylhexanoic acid, 4.4-dimethylhexanoic acid, 5,5-dimethylhexanoic acid, 2-ethylhhexanoic acid, 3-ethylhhexanoic acid, 4-ethylhhexanoic acid, 2-propylpentanoic acid, nonanoic acid, 1-methyloctanoic acid, 2-methyloctanoic acid, 3-methyloctanoic acid, 4-methyloctanoic acid, 5-methyloctanoic acid, 6-methyloctanoic acid, 7-methyloctanoic acid, 2,2-dimethylheptanoic acid, 2,3-dimethylheptanoic acid, 2,4-dimethylheptanoic acid, 2,5-dimethylheptanoic acid, 3,3-dimethylheptanoic acid, 4,4-dimethylheptanoic acid, 5,5-dimethylheptanoic acid, 2-ethyl-2-methylhexanoic acid, 3-ethyl-3-methylhexanoic acid, 4-ethyl-4-methylhexanoic acid, 5,5-dimethylheptanoic acid, 2,2,5-trimethylhexanoic acid, 2,2,4-trimethylhexanoic acid, 2,2,3-trimethylhexanoic acid, 2,4,4-trimethylhexanoic acid, 2,5,5-trimethylhexanoic acid, 2-propylhexanoic acid, 3-propylhexanoic acid, 3-isopropylhexanoic acid, 2-isopropylhexanoic acid, 4-ethyl-5-methylhexanoic acid, 5,6-dimethylheptanoic acid, 2,3,4-trimethylhexanoic acid, 2,3,5-trimethylhexanoic acid, 3,4,5-trimethylhexanoic acid, 2-isopropyl-3,3-dimethylbutanoic acid, 2-(tert-butyl)pentanoic acid, 3-ethyl-4,4-dimethylpentanoic acid, 4,4,5-trimethylhexanoic acid, 3-ethyl-3,4-dimethylpentanoic acid, 2-isopropyl-2-methylpentanoic acid, decanoic acid, 2-methylnonanoic acid, 3-methylnonanoic acid, 4-methylnonanoic acid, 5-methylnonanoic acid, 6-methylnonanoic acid, 7-methylnonanoic acid, 8-methylnonanoic acid, 2,2-dimethyloctanoic acid, 3,3-dimethyloctanoic acid, 4,4-dimethyloctanoic acid, 5,5-dimethyloctanoic acid, 6,6-dimethyloctanoic acid, 7,7-dimethyloctanoic acid, 2,2,3-trimethylheptanoic acid, 2,2,4-trimethylheptanoic acid, 2,2,5-trimethylheptanoic acid, 2,2,6-trimethylheptanoic acid, 2,3,3-trimethylheptanoic acid, 2,4,4-trimethylheptanoic acid, 2,5,5-trimethylheptanoic acid, 2,6,6-trimethylheptanoic acid, 3,3,4-trimethylheptanoic acid, 3,3,5-trimethylheptanoic acid, 3,3,6-trimethylheptanoic acid, 4,5,5-trimethylheptanoic acid, 4,6,6-trimethylheptanoic acid, 5,6,6-trimethylheptanoic acid, 2,3,4,5-tetramethylhexanoic acid, 2-ethyl-3,4-dimethylhexanoic acid, 4-ethyl-2,3-dimethylhexanoic acid, 3-ethyl-2,4-dimethylhexanoic acid, 2,3,4- trimethylheptanoic acid, 2-isopropyl-3,3-dimethylpentanoic acid, 2-isopropyl-3,4-dimethylpentanoic acid, 2,3-diethyl-4-methylpentanoic acid, 2,2-diethyl-4-methylpentanoic acid, 3,3-diethyl-4-methylpentanoic acid, 2-ethyl-2-isopropyl-pentanoic acid, 2-ethyl-2-isopropyl-3-methylbutanoic acid, 3-isopropyl-3,4-dimethylpentanoic acid, 3-ethyl-3,4,4-trimethylpentanoic acid, 2,2-diethyl-3,3-dimethylbutanoic acid, 2-isopropyl-2,3,3-trimethylbutanoic acid, maleic acid, fumaric acid and combinations thereof. In one aspect of this embodiment, the one or more water resistivity enhancers includes one or more of propionic acid, n-butyric acid, isobutyric acid, t-butylacetic acid, pentanoic acid, hexanoic acid, heptanoic acid, octanoic acid, nonanoic acid, decanoic acid, maleic acid, fumaric acid and combinations thereof. In one aspect of this embodiment, the one or more water resistivity enhancers includes pentanoic acid. In another aspect of this embodiment, the one or more water resistivity enhancers includes isobutyric acid. In another aspect of this embodiment, the one or more water resistivity enhancers includes 2-methylbutyric acid. In another aspect of this embodiment, the one or more water resistivity enhancers includes propionic acid.

In one embodiment, the amount of the water resistivity enhancer is from about 1 wt % to about 15 wt % of the formulation. In a further aspect of this embodiment, the amount of the water resistivity enhancer is from about 2 wt % to about 10 wt % of the formulation. In a further aspect of this embodiment, the amount of the water resistivity enhancer is from about 3 wt % to about 8 wt % of the formulation. In a further aspect of this embodiment, the amount of the water resistivity enhancer is from about 4 wt % to about 6 wt % of the formulation. In a further aspect of this embodiment, the amount of the water resistivity enhancer is from about 5 wt % to about 6 wt % of the formulation. In a further aspect of this embodiment, the amount of the water resistivity enhancer is about 5 wt % of the formulation. In a further aspect of this embodiment, the amount of the water resistivity enhancer is about 5.6 wt % of the formulation. In a further aspect of this embodiment, the amount of the water resistivity enhancer is about 6 wt % of the formulation.

In one embodiment, the formulation includes about 0.1 wt % to about 2.0 wt % of the one or more water resistivity enhancer.

In one embodiment, the formulation includes about 0.1 wt % to about 1.0 wt % of the one or more water resistivity enhancer.

In one embodiment, the formulation includes about 0.1 wt % to about 0.5 wt % of the one or more water resistivity enhancer.

In one embodiment, the formulation includes about 0.1 wt % to about 0.75 wt % of the one or more water resistivity enhancer.

In one embodiment, the formulation includes about 1.0 wt % to about 2.0 wt % of the one or more water resistivity enhancer.

In one embodiment, the formulation includes about 1.0 wt % to about 1.5 wt % of the one or more water resistivity enhancer.

In one embodiment, the formulation includes about 1.5 wt % to about 2.0 wt % of the one or more water resistivity enhancer.

In one embodiment, the formulation includes about 0.1 wt % of the one or more water resistivity enhancer.

In one embodiment, the formulation includes about 0.2 wt % of the one or more water resistivity enhancer.

In one embodiment, the formulation includes about 0.3 wt % of the one or more water resistivity enhancer.

In one embodiment, the formulation includes about 0.4 wt % of the one or more water resistivity enhancer.

In one embodiment, the formulation includes about 0.5 wt % of the one or more water resistivity enhancer.

In one embodiment, the formulation includes about 0.6 wt % of the one or more water resistivity enhancer.

In one embodiment, the formulation includes about 0.7 wt % of the one or more water resistivity enhancer.

In one embodiment, the formulation includes comprises about 0.8 wt % of the one or more water resistivity enhancer.

In one embodiment, the formulation includes comprises about 0.9 wt % of the one or more water resistivity enhancer.

In one embodiment, the formulation includes about 1.0 wt % of the one or more water resistivity enhancer.

In one embodiment, the formulation includes about 1.1 wt % of the one or more water resistivity enhancer.

In one embodiment, the formulation includes about 1.2 wt % of the one or more water resistivity enhancer.

In one embodiment, the formulation includes about 1.3 wt % of the one or more water resistivity enhancer.

In one embodiment, the formulation includes about 1.4 wt % of the one or more water resistivity enhancer.

In one embodiment, the formulation includes comprises about 1.5 wt % of the one or more water resistivity enhancer.

In one embodiment, the formulation includes about 1.6 wt % of the one or more water resistivity enhancer.

In one embodiment, the formulation includes about 1.7 wt % of the one or more water resistivity enhancer.

In one embodiment, the formulation includes about 1.8 wt % of the one or more water resistivity enhancer.

In one embodiment, the formulation includes about 1.9 wt % of the one or more water resistivity enhancer.

In one embodiment, the formulation includes about 2.0 wt % of the one or more water resistivity enhancer.

In one embodiment, the formulation includes about 0.1 wt % to about 2.0 wt % of isobutyric acid.

In one embodiment, the formulation includes about 0.1 wt % to about 1.0 wt % of isobutyric acid.

In one embodiment, the formulation includes about 0.1 wt % to about 0.5 wt % of isobutyric acid.

In one embodiment, the formulation includes about 0.2 wt % isobutyric acid.

In one embodiment, the formulation includes about 0.3 wt % of isobutyric acid.

In one embodiment, the formulation includes about 0.4 wt % of isobutyric acid.

In one embodiment, the formulation includes about 1.6 wt % of isobutyric acid.

In one embodiment, the formulation includes about 1.7 wt % of isobutyric acid.

In one embodiment, the formulation includes about 1.8 wt % of isobutyric acid.

In one embodiment, the formulation includes about 0.1 wt % to about 2.0 wt % of propionic acid.

In one embodiment, the formulation includes about 0.1 wt % to about 1.0 wt % of propionic acid.

In one embodiment, the formulation includes about 0.1 wt % to about 0.5 wt % of propionic acid.

In one embodiment, the formulation includes about 0.2 wt % propionic acid.

In one embodiment, the formulation includes about 0.3 wt % of propionic acid.

In one embodiment, the formulation includes about 0.4 wt % of propionic acid.

In one embodiment, the formulation includes about 0.1 wt % to about 2.0 wt % of 2-methylbutyric acid.

In one embodiment, the formulation includes about 0.1 wt % to about 1.0 wt % of 2-methylbutyric acid.

In one embodiment, the formulation includes about 0.1 wt % to about 0.5 wt % of 2-methylbutyric acid.

In one embodiment, the formulation includes about 0.2 wt % 2-methylbutyric acid.

In one embodiment, the formulation includes about 0.3 wt % of 2-methylbutyric acid.

In one embodiment, the formulation includes about 0.4 wt % of 2-methylbutyric acid.

III. Method of Preparing ZPPA-Based Films

Another aspect of the disclosed and claimed subject matter relates to the use of ZPPA and formulations thereof to form ZrOx films.

Solutions including ZPPA can be coated on a substrate using techniques well known to those skilled in the art, such as dipping, spin coating or spraying. Preferably the solutions are spin coated. The film thickness of the underlayer coating ranges from about 5 nm to about 400 nm, preferably about 10 nm to about 120 nm. The coating is further heated on a hot plate or convection oven for a sufficient length of time to remove any residual solvent and induce curing, and thus insolubilizing the antireflective coating to prevent intermixing between the antireflective coating and the layer to be coated above it. The preferred temperatures are generally below about 450° C., and can range, for example, from about 90° C. to about 300° C., or about 160° C. to about 250° C. The coating may be coated over other layer or layers of antireflective coating(s), such as a high carbon (greater than about 80% or about 85% or about 90%) content antireflective coating.

The substrates over which the underlayer coating is formed can be any of those typically used in the semiconductor industry. Suitable substrates include, without limitation, low dielectric constant materials, silicon, silicon substrate coated with a metal surface, copper coated silicon wafer, copper, aluminum, polymeric resins, silicon dioxide, metals, doped silicon dioxide, silicon nitride, tantalum, polysilicon, ceramics, aluminum/copper mixtures; gallium arsenide and other such Group III/V compounds. The substrate may also be other antireflective coatings or underlayers, such as high carbon underlayers coated over the above-mentioned substrates. The substrate may comprise any number of layers made from the materials described above.

A film of photoresist can be coated on top of the underlayer coating and baked to substantially remove the photoresist solvent. An edge bead remover may be applied after the coating steps to clean the edges of the substrate using processes well known in the art. Photoresists can be any of the types used in the semiconductor industry, provided the photoactive compound in the photoresist and the antireflective coating substantially absorb at the exposure wavelength used for the imaging process. Photoresists useful for immersion lithography are preferred. Typically, photoresists suitable for imaging with immersion lithography may be used, where such photoresists have a refractive index higher than 1.85 and also are hydrophobic having water contact angle in the range of about 75° to about 95°.

There are several major deep ultraviolet (uv) exposure technologies that have provided significant advancement in miniaturization, and these radiation of 248 nm, 193 nm and 13.5 nm. Chemically amplified photoresists are often used. Photoresists for 248 nm have typically been based on substituted polyhydroxystyrene and its copolymers/onium salts, such as those described in U.S. Pat. Nos. 4,491,628 and 5,350,660. On the other hand, photoresists for exposure at 193 nm and 157 nm require non-aromatic polymers since aromatics are opaque at this wavelength. U.S. Pat. Nos. 5,843,624 and 6,866,984 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon to hydrogen ratios which improve etch resistance, they also provide transparency at low wavelengths and they have relatively high glass transition temperatures. U.S. Pat. No. 5,843,624 discloses polymers for photoresist that are obtained by free radical polymerization of maleic anhydride and unsaturated cyclic monomers. Any of the known types of 193 nm photoresists may be used, such as those described in U.S. Pat. Nos. 6,447,980 and 6,723,488 which are hereby incorporated herein by reference. Photoresists that absorb extreme ultraviolet radiation (EUV) of 13.5 nm are also useful and are known in the art. Thus, photoresists absorbing in the range of about 12 nm to about 250 nm are useful. The novel coatings can also be used in process with nanoimprinting and e-beam resists.

After the coating process, the photoresist can be image wise exposed. The exposure may be done using typical exposure equipment. The exposed photoresist is then developed in an aqueous developer to remove the treated photoresist. The developer is preferably an aqueous alkaline solution including, for example, tetramethylammonium hydroxide (TMAH), typically 2.38 wt % TMAH. The developer may further include surfactant(s). An optional heating step can be incorporated into the process prior to development and after exposure.

The process of coating and imaging photoresists is well known to those skilled in the art and is optimized for the specific type of photoresist used. The photoresist patterned substrate can then be dry etched with an etching gas or mixture of gases, in a suitable etch chamber to remove the exposed portions of the underlayers and optional other antireflective coatings. Various etching gases are known in the art for etching underlayer coatings, such as those comprising $O_2$, $CF_4$, $CHF_3$, $Cl_2$, HBr, $SO_2$, CO, etc. In one embodiment, the article comprises a semiconductor substrate with a high carbon antireflective film, over which the novel zirconium underlayer is coated. A photoresist layer is coated above this. The photoresist is imaged as disclosed above and the underlayer is dry etched using gases comprising fluorocarbons. After the underlayer is etched, the high carbon film can be dry etched using oxygen or oxygen mixtures.

In one embodiment, ZPPA and ZPP formulation thereof may be applied to a substrate with the following steps:

a. ZPPA or ZPP formulation is poured on a silicon substrate and spin coated with the spin speed is adjusted to give desired thickness; and
b. the coated silicon wafer is baked on a hotplate at different temperature and for different periods of time vary depending on desired properties.

In one embodiment, the baking temperature is approximately 200 C to 600 C and baking time 30 sec to 1 hr are selected. Typically baking temperature is 250° C. to approximately 500° C. and the baking time is approximately 60 sec. to approximately 300 sec.

In another embodiment, the baking may be single step bake or multiple step bake (e.g. baking at approximately 250° C./approximately 60 sec, then approximately 450° C./approximately 120 sec).

EXAMPLES

Reference will now be made to more specific embodiments of the present disclosure and experimental results that provide support for such embodiments. The examples are given below to more fully illustrate the disclosed subject matter and should not be construed as limiting the disclosed subject matter in any way.

It will be apparent to those skilled in the art that various modifications and variations can be made in the disclosed subject matter and specific examples provided herein without departing from the spirit or scope of the disclosed subject matter. Thus, it is intended that the disclosed subject matter, including the descriptions provided by the following examples, covers the modifications and variations of the disclosed subject matter that come within the scope of any claims and their equivalents.

Materials and Methods

The reactions were conducted under air/moisture free environment. Propionic acid (Millipore Sigma), propionic anhydride (Millipore Sigma) and 1-methoxy-2-propanol (PGME; EMD Performance Materials) were kept over molecular sieves (3 Å) and were then distilled under an inert atmosphere and atmospheric pressure.

A SuperNova (Oxford Diffraction) Diffractometer with Atlas CCD Detector was used to determine X-Ray crystallography structure. Radiation: Cu Ka (1.5418 Å); monochromator: X-ray mirrors; measuring software: CrysAlisPro 39.46; evaluation software: $OLEX^2$ 1.2.8.

The simultaneous thermal analysis (STA) was carried out on an STA 449 F3 Jupiter from Netzsch Geratebau GmbH with a heating rate of 10° C./min from 30° C. to 1000° C. under inert and air conditions.

Dynamic light scattering (DLS) measurements used to measure ZPP and ZPPA sizes were performed at 25° C. using a Malvern Zetasizer Nano-S—Model No. ZEN1600.

A Tokyo Electron Ltd Clean Track ACT 8, ACT 12 or Mark 8 was used for Coating and baking of ZPPA or ZPP formulations. C, H and Zr content (wt %) were determined by Elemental Analysis by Intertek of Whitehouse, NJ.

The refractive index (n) and the extinction coefficient (k) were measured on a J. A. Woollam VUV-VASE VU-302 Spectroscopic Ellipsometer. Samples were coated on Si wafer at target film thickness and baked at 250° C./60 sec+450° C./90 sec and measured the optical parameters.

Bulk etch rates were measured using TRION DUAL CHAMBER MINILOCK III as follows. ZPPA or ZPP formulation was spin coated on a silicon wafer, baked at 250° C./60 sec+450° C./90 sec. Spin speed was adjusted to desired film thickness. The coated coupon wafers were loaded into the Trion etcher and etched setting Ar 80 sccm, CF4 20 sccm, Pressure 50mT, Top RF 1000 W, Bot RF 400 W, Etch time 120 sec. The film thickness of the coupons was measured before and after the etching and bulk etch rate was obtained.

XPS measurements were performed on Thermo Fisher Scientific—K-Alpha X-ray Photoelectron Spectrometer (XPS), KA1191 using the following testing protocol: The wafers were coated with the MHM at target film thickness and baked at 250° C./60 sec+450° C./90 sec. The wafers were then submitted for XPS analysis. Depending on the film thickness of each wafer, after XPS measurement completed, Ar Sputtering rate and atomic % is be reported.

Moisture sensitivity was evaluated using Humidity control chamber (Ets Electro-tech systems Inc). Samples in glass vials were put inside the humidity chamber box at 45% RH, opened inside the chamber and observed changes for 24 hr.

Contact angles in water were measured using Data Physics Contact Angle measurement system, OCA 20L.

I. Zirconium Propionate Polymorph S1 (ZPPA) and Related Compounds

A. Synthesis 1 of Zirconium Propionate Polymorph S1 (ZPPA)

The reaction was conducted under air/moisture free environment. Propionic acid (Millipore Sigma), propionic anhydride (Millipore Sigma) and 1-methoxy-2-propanol (PGME; EMD Performance Materials) were kept over molecular sieves (3 Å) and were then distilled under an inert atmosphere and atmospheric pressure. The propionic acid (19.48 g; 0.263 mol) was added to propionic anhydride (103.08 g, 0.792 mol) all at once and the mixture was stirred continuously for 2 minutes. Thereafter, 100.93 g (0.263 mol) zirconium (IV) $(tert\text{-}butoxide)_4$ (Millipore Sigma) was added dropwise over 45 minutes. During this addition, the temperature was controlled to bring it to approximately to 60° C. The mixture was then stirred at 62-65° C. for 18 hours. Thereafter, 118.50 g (1.315 mol) of 1-methoxy-2-propanol was added by portion into the solution, and the crude ZPPA was stirred for an additional 5 hours at 62° C. The mixture was transferred to a dry round bottom flask filled with nitrogen. The flask was placed onto a vacuum rotary evaporator with a heating bath to distill out the volatile components. Removal of volatiles gave 81.9 g of the solid with residual PGME (~20% by 1H NMR). The PGME was removed by drying in a vacuum oven at 90° C. for 3 days.

The ZPPA characteristics are described above.

B. Synthesis 2 of Zirconium Propionate Polymorph S2

Zirconium (IV) $(tert\text{-}butoxide)_4$ (32.65 g; 0.085 mol) was added to 2-methylpropanoic acid (7.50 g; 0.085 mol) and propionic anhydride (33.22 g; 0.255 mol) over 34 min then stirred for 20 hours, followed with the addition of 1-methoxy-2-propanol (22.9 g; 0.254 mol) as described in Example 1. 27.43 g of zirconium (IV) isobutyrato-propionate solid solvate I with residual volatiles of 6.92% wt. was obtained.

C. Synthesis 3 of Zirconium Propionate Polymorph S3

Zirconium (IV) $(tert\text{-}butoxide)_4$ (27.48 g; 0.0716 mol) was added to 2-methylpropanoic acid (12.94 g; 0.146 mol), and propionic anhydride (27.85 g; 0.214 mol) over 25 min then stirred for 20 hours, followed with the addition of 1-methoxy-2-propanol (12.96 g; 0.144 mol) as described in Example 1. 22.92 g of zirconium (IV) isobutyrato-propionate solid solvate II with residual volatiles of 11.33% wt. was obtained.

D. Synthesis 4 of Zirconium Propionate Polymorph S4

Zirconium (IV) (tert-butoxide)$_4$ (19.77 g; 0.0515 mol) was added to methacrylic acid (4.43 g; 0.0515 mol), and propionic anhydride (19.97 g; 0.153 mol) over 41 min then stirred for 20 hours, followed with the addition of 1-methoxy-2-propanol (13.96 g; 0.155 mol) as described in Example 1. 17.28 g of Zirconium (IV) methacrylato-propionate solid solvate with residual volatiles of 21.7% wt. was obtained.

E. Synthesis 5 of Zirconium Propionate Polymorph S5

Zirconium (IV) (tert-butoxide)$_4$ (28.43 g; 0.074 mol) was added to 2-(2-methoxyethoxy)acetic acid (9.94 g; 0.074 mol) and propionic anhydride (28.93 g; 0.222 mol) over 52 min then stirred for 18 hours as described in Example 1. 30.7 g of zirconium (IV) 2-(2-methoxyethoxy)acetato-propionate as glass like solvate with residual volatiles of 17.24% wt. was obtained.

F. Synthesis 6 of Zirconium Propionate Polymorph S6

Zirconium (IV) (tert-butoxide)$_4$ (24.24 g; 0.0618 mol) was added to 2-[2-(2-methoxyethoxy)ethoxy]acetic acid (11.26 g; 0.063 mol) and propionic anhydride (24.67 g; 0.190 mol) over 35 min then stirred for 22 hours as described in Example 1. 30.7 g of zirconium (IV) 2-[2-(2-methoxyethoxy)ethoxy]acetato-propionate as low temperature melting solvate with residual volatiles of 28.58% wt. was obtained.

G. Synthesis 7 of Zirconium Propionate Polymorph S7

Zirconium (IV) (tert-butoxide)$_4$ (30.11 g; 0.0785 mol) was added to benzoic acid (9.77 g; 0.08 mol), and propionic anhydride (30.79 g; 0.236 mol) over 29 min then stirred for 19.7 hours, followed with the addition of 1-methoxy-2-propanol (21.36 g; 0.237 mol) as described in Example 1. 29.08 g of zirconium (IV) benzoato-propionate solvate with residual volatiles of 19.8% wt. was obtained.

H. Synthesis 8 of Zirconium Propionate Polymorph S8

Zirconium (IV) (tert-butoxide)$_4$ (31.43 g; 0.082 mol) was added to 4-methoxybenzoic acid (8.97 g; 0.059 mol) and propionic anhydride (31.24 g; 0.240 mol) over 53 min then stirred for 21 hours as described in Example 1. 35.15 g of zirconium (IV) 4-methoxybenzoato-propionate as glassy solvate with residual volatiles of 16.71% wt. was obtained.

I. Synthesis 9 of Zirconium Propionate Polymorph S9

Zirconium (IV) (tert-butoxide)$_4$ (24.37 g; 0.0635 mol) was added to phenylacetic acid (8.69 g; 0.0638 mol) and propionic anhydride (24.73 g; 0.19 mol) over 50 min then stirred for 19 hours, followed with the addition of 1-methoxy-2-propanol (17.17 g; 0.0.191 mol) as described in Example 1. 23.95 g of zirconium (IV) phenylacetato-propionate as glass like solvate with residual volatiles of 5.6% wt. was obtained.

J. Synthesis 10 of Zirconium Propionate Polymorph S10

Zirconium (IV) (tert-butoxide)$_4$ (19.44 g; 0.0507 mol) was added to propionic anhydride (19.78 g; 0.152 mol) over 44 min then stirred for 15.5 hours, followed with the addition of DI water (1.11 g; 0.062 mol) then stirred as in Example 1. 12.71 g of zirconium (IV) hydroxo-propionate solid solvate with residual volatiles of 13.1% wt. was obtained.

II. Synthesis of THTPM Tris-Propionate (THTPM-TP)

A. Reaction in Solvent Synthesis 4,4',4"-Trihydroxytriphenylmethane (THTPM, 5.04 g, 17.24 mmol) and propionic anhydride (13.46 g, 103.44 mmol) were refluxed in toluene (50 ml) for 6.5 hours that $^1$H NMR (DMS-d6) showed the reaction was completed. After cooling to room temperature, volatiles were removed from the crude by distilling using a rotary evaporator. Removal of volatiles gave 7.9 g of solid which was then crystallized from 25.8 g of isopropanol. After drying in the vacuum oven at 95° C., 7.39 g (93.1% yield) of the tri-ester as the greenish crystalline powder was obtained.

B. Solvent Free Synthesis 4,4',4"-Trihydroxytriphenylmethane (THTPM, 3.03 g, 10.36 mmol) and propionic anhydride (7.19 g, 55.25 mmol) were stirred at 120° C. for 6.5 hours. After cooling to room temperature, the crude was poured into 400 mL of DI water and the resulting crystalline material was recovered by filtration the next day. After drying in the vacuum oven at 95° C., 4.53 g (94.9% yield) with purity of 95.6% by $^1$H NMR (DMS-d6) was obtained.

Characterization: MP 100.7° C.; $^1$H NMR (400 Mz, $CDCl_3$) δ 7.08 (d, J=8.54 Hz, 6H, Ar—H), 6.99 (d, J=8.54 Hz, 6H, Ar—H), 5.51 (s, 1H, C—H), 2.56 (q, J=7.48 Hz, 6H, C—$H_2$), 1.24 (t, J=7.48 Hz, 9H, C—$H_3$) ppm; $^{13}$C NMR (400 Mz, $CDCl_3$) δ 172.9, 149.4, 140.9, 130.3, 121.5, 55.1, 27.8, 9.1 ppm; FTIR (KBr) 3044, 2982, 2944, 2882, 1756, 1604, 1593, 1505, 1462, 1417, 1357, 1269 $cm^{-1}$. Analysis Calculated for $C_{28}H_{28}O_6$: C, 73.03, H, 6.13; Found: C, 72.86, H, 6.06.

III. Exemplified Formulations

ZPPA Formulations

A. Formulation 1

A formulation including ZPPA was prepared by mixing (i) 246.8 g of a 15.4% ZPPA solution in ArF Thinner, (ii) 2 g of isobutyric acid (Millipore Sigma), (iii) 4 g of 4,4',4"-trihydroxytriphenylmethane (Asahi Yukizai), (iv) 8.25 g of 10% X22-4952 (ShinEtsu) solution in AZ® ArF Thinner and (v) 289 g of AZ® ArF Thinner. The components were mixed overnight and then filtered through a 0.2 μm filter.

Performance: Film uniformity (3 sigma %) 3.8; Etch rate (A/sec) 1.37; and Moisture resistance (h) 15. Refractive index (n) and the extinction coefficient (k): n 2.44, k 0.54 at 193 nm, n 2.11, k 0.03 at 248 nm.

B. Formulation 2

A formulation including ZPPA was prepared by mixing (i) 388.6 g of a 15.4% ZPPA solution in ArF Thinner, (ii) 1.43 g of isobutyric acid (Millipore Sigma), (iii) 28.64 g of a 10% 4,4',4"-trihydroxytriphenylmethane (Asahi Yukizai) solution in ArF Thinner, (iv) 6.75 g of a 10% X22-4952 (ShinEtsu) solution in AZ® ArF Thinner, (v) 12.56 g of gamma-valerolactone and (vi) 12 g of AZ® ArF Thinner. The components were mixed overnight and then filtered through a 0.2 μm filter.

Performance: Film uniformity (3 sigma %) 3.5; Etch rate (A/sec) 1.38; and Moisture resistance (h) 13. Refractive index (n) and the extinction coefficient (k): n 2.49, k 0.60 at 193 nm, n 2.15, k 0.03 at 248 nm.

ZPP Formulations

The ZPP used in these formulations has an average molecular weight of about 4,000 Da to about 10,000 Da.

C. Formulation 3

32.39 g of ZPP, 2 g of isobutyric acid (Millipore Sigma), 3.409 g of 4,4',4"-trihydroxytriphenyl-methane (Asahi Yukizai) and 7.5 g of 10% X22-4952 (ShinEtsu) were combined with 455 g of AZ® ArF Thinner. The solution was mixed overnight and then filtered through a 0.2 μm filter.

Performance: Film uniformity (3 sigma %) 3.6; Etch rate (A/sec) 1.34; and Moisture resistance (h) 12. Refractive index (n) and the extinction coefficient (k): n 2.55, k 0.63 at 193 nm, n 2.20, k 0.04 at 248 nm.

D. Formulation 4

431.8 g of ZPP, 17.05 g of isobutyric acid (Millipore Sigma), 454.55 g of 10% 4,4',4"-trihydroxytriphenylmethane (Asahi Yukizai), 80 g of 10% X22-4952 (ShinEtsu) and 285 g of gamma-valerolactone were combined with 8.656 kg of AZ® ArF Thinner. The solution was mixed overnight and then filtered through a 0.2 μm filter.

Performance: Film uniformity (3 sigma %) 3.7; Etch rate (A/sec) 1.36; and Moisture resistance (h) 12. Refractive index (n) and the extinction coefficient (k): n 2.53, k 0.62 at 193 nm, n 2.19, k 0.03 at 248 nm.

E. Formulations 5-45

Additional exemplary formulations are described in Tables 6-9. In these examples, the Zr material, etch resistance modulator additive, one or more solvents, surfactant and water resistivity enhancers are mixed overnight and then filtered through a 0.2 μm filter.

TABLE 6

| Ingredient (wt %) | | Ex. 5 | Ex. 6 | Ex. 7 | Ex. 8 | Ex. 9 | Ex. 10 | Ex. 11 | Ex.12 |
|---|---|---|---|---|---|---|---|---|---|
| Zr Material | ZPPA | — | — | 4.42 | — | 5.46 | 5.46 | — | 5.46 |
| | ZPP | 5.42 | 5.29 | — | 5.46 | — | — | 5.42 | — |
| Etch | THTPM | 0.57 | 0.56 | 0.47 | 0.57 | 0.57 | — | — | — |
| Resistance Modulator Additive | THTPM-TP | — | — | — | — | — | 0.57 | 0.57 | 0.57 |
| Solvent(s) | ArF Thinner | 93.63 | 92.36 | 94.73 | 93.53 | 93.53 | 93.53 | 93.63 | — |
| | PGMEA | — | — | — | — | — | — | — | 93.63 |
| Surfactant | X22-4952 | 0.10 | 0.10 | 0.15 | 0.15 | 0.15 | 0.15 | 0.10 | 0.10 |
| Water Resistivity Enhancer | IBA | 0.29 | 1.69 | 0.23 | 0.29 | 0.29 | 0.29 | 0.29 | 0.29 |
| Performance | Film Uniformity (3 sigma %) | 3.6 | 3.7 | 3.8 | 3.5 | 3.9 | 4 | 4.1 | 3.9 |
| | Etch Rate (A/sec) | 1.36 | 1.36 | 1.37 | 1.23 | 1.26 | 1.13 | 1.15 | 1.2 |
| | Moisture Resistance (h) | 12 | 24 | 15 | 13 | 16 | 16 | 18 | 18 |

TABLE 7

| Ingredient (wt %) | | Ex. 13 | Ex. 14 | Ex. 15 | Ex. 16 | Ex. 17 | Ex. 18 | Ex. 19 | Ex.20 |
|---|---|---|---|---|---|---|---|---|---|
| Zr Material | ZPPA | — | — | — | — | — | — | — | — |
| | ZPP | 5.42 | 5.46 | 5.46 | 5.46 | 5.46 | 5.46 | 5.46 | 5.46 |
| Etch | THTPM | — | 0.56 | — | — | — | — | 0.56 | 0.56 |
| Resistance | THTPM-TP | 0.57 | — | — | — | — | — | — | — |
| Modulator | NF0327 | — | — | 0.57 | — | — | — | — | — |
| Additive | NF0A28 | — | — | — | 0.57 | — | — | — | — |
| | NF71A7 | — | — | — | — | 0.57 | — | — | — |
| | NF0127 | — | — | — | — | — | 0.57 | — | — |
| Solvent(s) | ArF Thinner | — | — | 94.73 | 93.53 | 93.53 | 93.53 | 93.53 | 93.53 |
| | PGMEA | 93.63 | 92.36 | — | — | — | — | — | — |
| Surfactant | X22-4952 | 0.10 | 0.10 | 0.15 | 0.15 | 0.15 | 0.15 | 0.10 | 0.10 |
| Water | IBA | 0.29 | 1.69 | 0.29 | 0.29 | 0.29 | 0.29 | — | — |
| Resistivity | PA | — | — | — | — | — | — | 0.29 | — |
| Enhancer | Acetic Acid | — | — | — | — | — | — | — | 0.29 |
| Performance | Film Uniformity (3 sigma %) | 3.9 | 4 | 3.7 | 3.8 | 3.8 | 3.6 | 3.8 | 3.9 |

TABLE 7-continued

| Ingredient (wt %) | | Ex. 13 | Ex. 14 | Ex. 15 | Ex. 16 | Ex. 17 | Ex. 18 | Ex. 19 | Ex.20 |
|---|---|---|---|---|---|---|---|---|---|
| | Etch Rate (A/sec) | 125 | 1.28 | 1.33 | 1.24 | 1.33 | 1.26 | 1.32 | 1.24 |
| | Moisture Resistance (h) | 14 | 26 | 15 | 16 | 16 | 14 | 10 | 8 |

TABLE 8

| Ingredient (wt %) | | Ex. 21 | Ex. 22 | Ex. 23 | Ex 24 | Ex. 25 | Ex. 26 | Ex. 27 | Ex. 28 | Ex. 29 | Ex. 30 |
|---|---|---|---|---|---|---|---|---|---|---|---|
| Zr Material | ZPP | 5.46 | 5.46 | 5.46 | 5.46 | 5.46 | 5.46 | 5.46 | 5.46 | 5.46 | 5.46 |
| Etch Resistance Modulator Additive | THTPM | 0.56 | 0.56 | 0.56 | 0.56 | 0.56 | 0.56 | 0.56 | 0.56 | 0.56 | 0.56 |
| Solvent(s) | ArF Thinner | 93.53 | 93.53 | 94.73 | 93.53 | 93.53 | 93.53 | 93.53 | 93.53 | 93.53 | 93.53 |
| Surfactant | XD22-4952 | — | — | — | 0.15 | 0.15 | 0.15 | 0.10 | 0.10 | — | — |
| | KF53 | 0.1 | 0.05 | 0.025 | — | — | — | — | — | — | — |
| | KF353A | — | — | — | 0.1 | 0.15 | 0.2 | 0.3 | — | — | — |
| | KP341 | — | — | — | — | — | — | — | 0.1 | 0.05 | 0.001 |
| Water Resistivity Enhancer | IBA | 0.29 | 0.29 | 0.29 | 0.29 | 0.29 | 0.29 | 0.29 | 0.29 | 0.29 | 0.29 |
| Performance | Film Uniformity (3 sigma %) | 7.2 | 7.3 | 9.3 | 7.1 | 5.2 | 4.8 | 4.5 | 10.5 | 11 | 13 |
| | Etch Rate (A/sec) | 1.35 | 1.28 | 1.29 | 1.25 | 1.32 | 1.23 | 1.15 | 1.25 | 1.31 | 1.38 |
| | Moisture Resistance (h) | 13 | 14 | 12 | 14 | 12 | 12 | 10 | 11 | 12 | 10 |

TABLE 9

| Ingredient (wt %) | | Ex. 37 | Ex. 38 | Ex. 39 | Ex. 40 | Ex. 41 | Ex. 42 | Ex. 43 | Ex. 44 | Ex. 45 |
|---|---|---|---|---|---|---|---|---|---|---|
| Zr Material | ZPPA S2 | 5.46 | — | — | — | — | — | — | — | — |
| | ZPPA S3 | — | 5.46 | — | — | — | — | — | — | — |
| | ZPPA S4 | — | — | 5.46 | — | — | — | — | — | — |
| | ZPPA S5 | — | — | — | 5.46 | — | — | — | — | — |
| | ZPPA S6 | — | — | — | — | 5.46 | — | — | — | — |
| | ZPPA S7 | — | — | — | — | — | 5.46 | — | — | — |
| | ZPPA S8 | — | — | — | — | — | — | 5.46 | — | — |
| | ZPPA S9 | — | — | — | — | — | — | — | 5.46 | — |
| | ZPPA S10 | — | — | — | — | — | — | — | — | 5.46 |
| Etch Resistance Modulator Additive | THPTM | 0.57 | 0.57 | 0.57 | 0.57 | 0.57 | 0.57 | 0.57 | 0.57 | 0.57 |
| Solvent(s) | ArF Thinner | 93.53 | 93.53 | 93.53 | 93.53 | 93.53 | 93.53 | 93.53 | 93.53 | 93.53 |
| Surfactant | X22-4952 | 0.10 | 0.10 | 0.10 | 0.10 | 0.10 | 0.10 | 0.10 | 0.10 | 0.10 |
| Water Resistivity Enhancer | IBA | 0.29 | 0.29 | 0.29 | 0.29 | 0.29 | 0.29 | 0.29 | 0.29 | 0.29 |
| Performance | Film Uniformity (3 sigma %) | 3.8 | 3.9 | 4.1 | 4.2 | 4.4 | 3.9 | 4.5 | 3.9 | 3.8 |
| | Etch Rate (A/sec) | 1.25 | 1.32 | 1.28 | 1.34 | 1.36 | 1.32 | 1.2 | 1.15 | 1.23 |
| | Moisture Resistance (h) | 14 | 16 | 17 | 14 | 13 | 14 | 14 | 15 | 14 |

V. Preparation and Performance of Films

As shown in examples 1-4 and 5-45, this invention provides spin on metal-organic formulations. All formulations in examples 1-45 are spin coatable and forms excellent etching resistance and Ar sputtering etch rate. Besides these formulations have good stability in moist environment.

All the formulations have good film thickness uniformity and 3 sigma % is <10% and 3.2-6.50%. Bulk etch rate is low 0.6~0.8 A/sec and good resistance under the condition. Ar sputtering rate is 1.2-~1.6 A/sec. Ar sputtering rate and bulk etch rate ration is generally high, >1.5 and good etching selectivity. The formulations are stable to moisture and did not show change >8 hours in moisture chamber.

Although the disclosed and claimed subject matter has been described and illustrated with a certain degree of particularity, it is understood that the disclosure has been made only by way of example, and that numerous changes in the conditions and order of steps can be resorted to by those skilled in the art without departing from the spirit and scope of the disclosed and claimed subject matter.

What is claimed is:

1. A formulation comprising:

(i) zirconium propionate (ZPP);

(ii) one or more etch resistance modulator additive comprising one or more of

A. 4,4′,4″-trihydroxytriphenylmethane (THTPM):

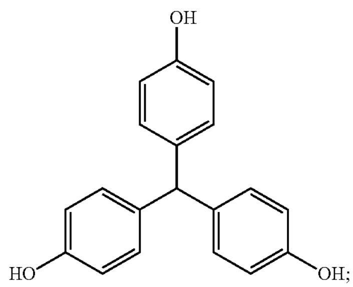

B. 4,4′,4″-tripropionyloxytriphenylmethane (THTPM-TP; $3D_1$):

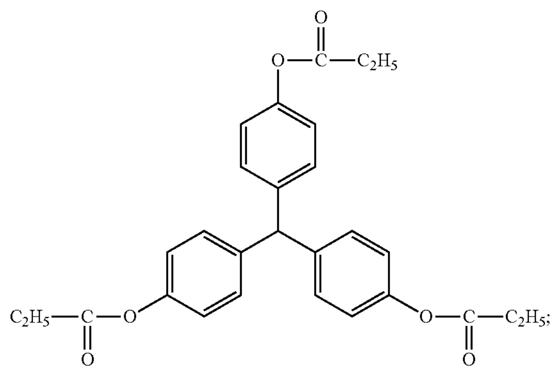

C. $3D_2$:

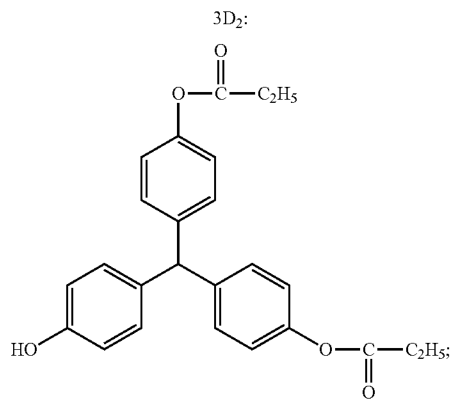

-continued

D. $3D_3$:

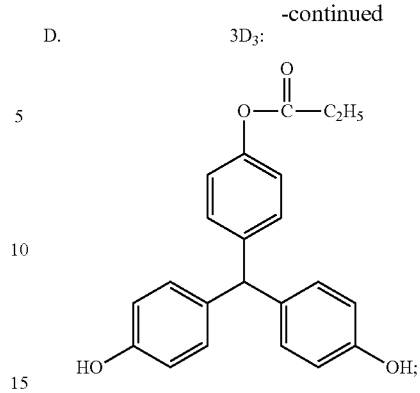

and

E. a compound of structure (1):

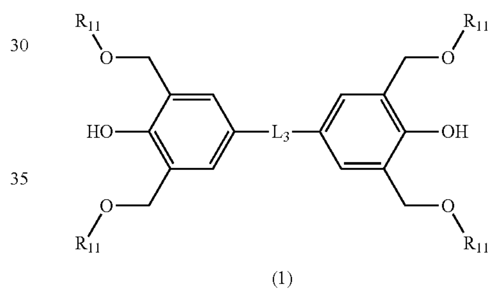

(1)

wherein $R_{11}$ is hydrogen or methyl; and $L_3$ is a direct bond, a substituted or unsubstituted $C_{1-3}$ alkyl, or a substituted or unsubstituted $C_{7-16}$ aralkyl;

(iii) one or more solvents, (iv) one or more surfactant; and (v) one or more water resistivity enhancer.

2. The formulation of claim 1, wherein the ZPP comprises ZPP assigned CAS No. 84057-80-7.

3. The formulation of claim 1, wherein the ZPP comprises $Zr(CH_3CH_2COO)_{4-x}(OH)_x$, where x=1–3.

4. The formulation of claim 1, wherein the ZPP comprises an oligomer or polymeric species including, in any sequence, the repeat units:

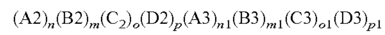

$$(A2)_n(B2)_m(C_2)_o(D2)_p(A3)_{n1}(B3)_{m1}(C3)_{o1}(D3)_{p1}$$

wherein each of n, n1, m, m1, o, o1, p and p1=0–10, a total of n, n1, m, m1, o, o1, p and p1 is between 2 and 10; and the repeat units are shown in the following table where "" represents an actual or potential direct valence bond from a protonated or unprotonated oxygen atom to another zirconium in an oligomer or polymeric zirconium complex, or alternatively a direct valence bond to H forming a Zr—OH moiety:

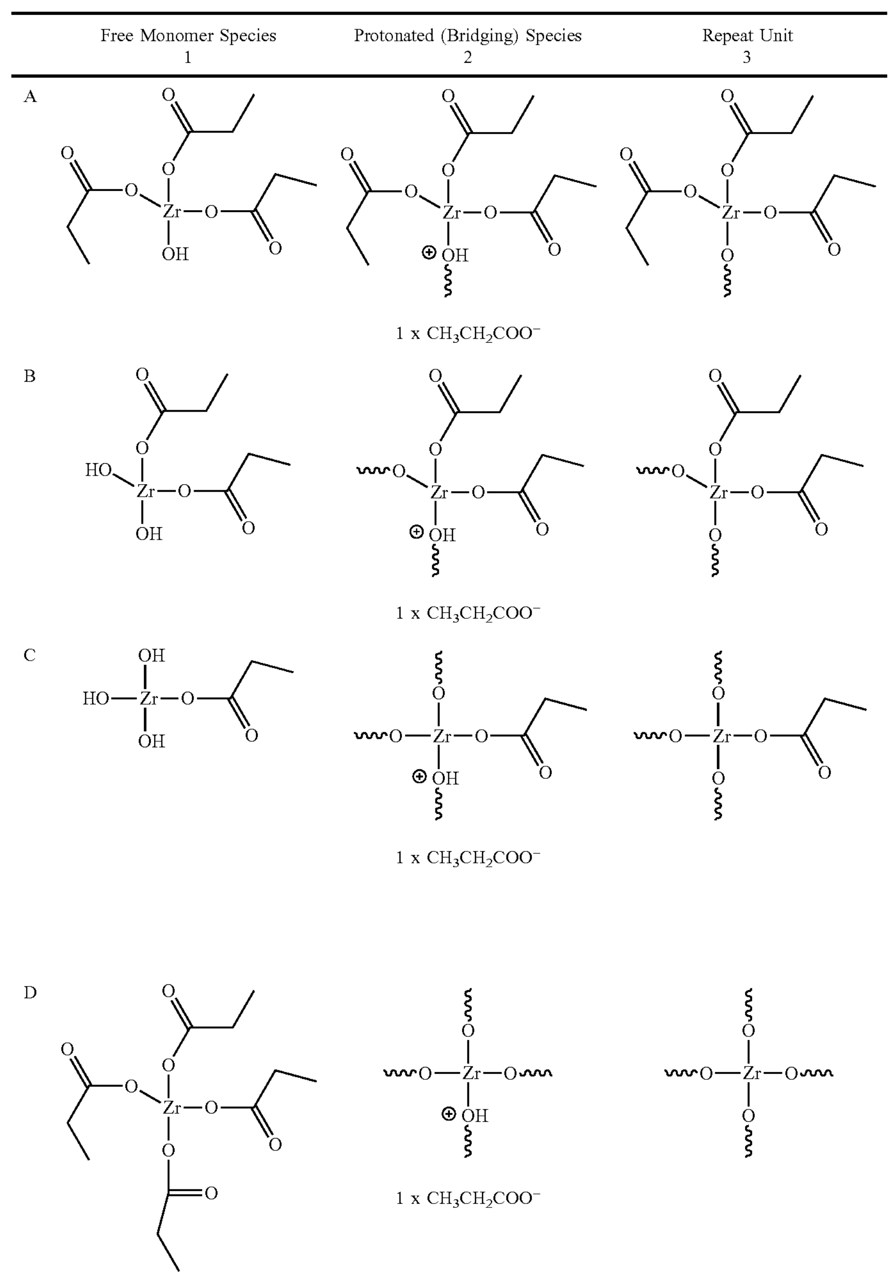

| | Free Monomer Species 1 | Protonated (Bridging) Species 2 | Repeat Unit 3 |
|---|---|---|---|
| A | | 1 x $CH_3CH_2COO^-$ | |
| B | | 1 x $CH_3CH_2COO^-$ | |
| C | | 1 x $CH_3CH_2COO^-$ | |
| D | | 1 x $CH_3CH_2COO^-$ | |

5. The formulation of claim 1, wherein the ZPP comprises an oligomer or polymeric species having hydroxyl group to propionate ligand ratio of about 0.5 to about 1.1 as measured by proton NMR.

6. The formulation of claim 1, wherein the ZPP comprises about 0.5 wt % to about 6 wt % of water.

7. The formulation of claim 1, wherein the ZPP comprises about 0.5 wt % to about 6 wt % of propionic acid.

8. The formulation of claim 1, wherein the ZPP has an average diameter (nm) of about 7.0 nm to about 12.0 nm as measured by dynamic light scattering (DLS).

9. The formulation of claim 1, wherein the (ii) one or more etch resistance modulator additive comprises a compound of structure (1):

(1)

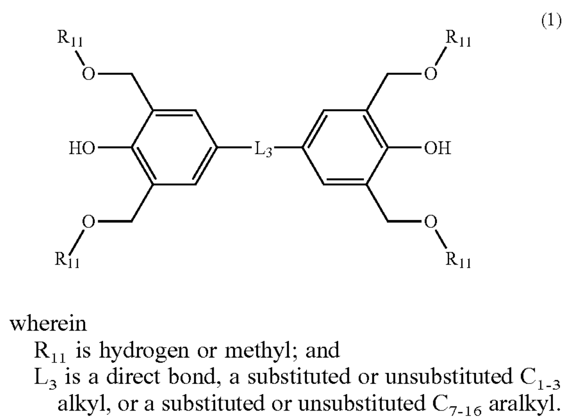

wherein $R_{11}$ is hydrogen or methyl; and $L_3$ is a direct bond, a substituted or unsubstituted $C_{1-3}$ alkyl, or a substituted or unsubstituted $C_{7-16}$ aralkyl.

10. The formulation of claim 1, wherein the (ii) one or more etch resistance modulator additive comprises one or more of:

A.

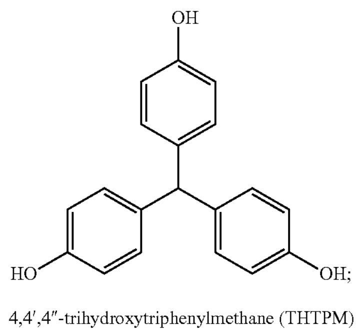

4,4′,4″-trihydroxytriphenylmethane (THTPM)

B.

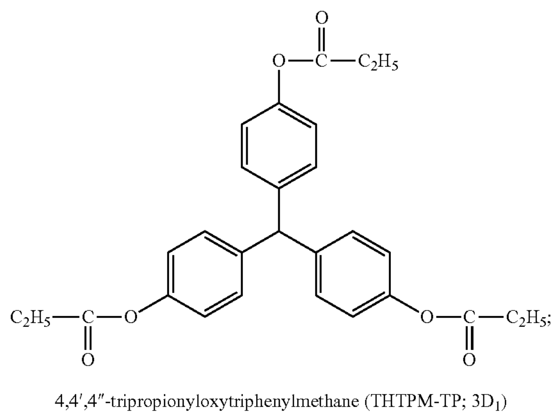

4,4′,4″-tripropionyloxytriphenylmethane (THTPM-TP; $3D_1$)

C.

$3D_2$

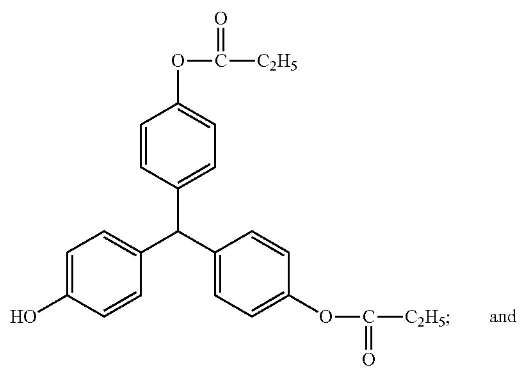

and

-continued

D.

$3D_3$

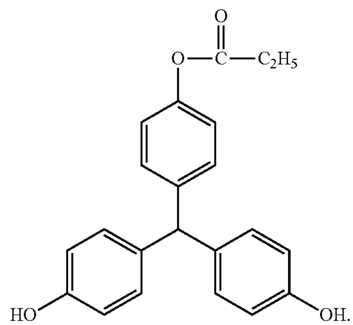

11. The formulation of claim 1, wherein the formulation comprises approximately 0.1 wt % to approximately 1 wt % of the (ii) one or more etch resistance modulator additive.

12. The formulation of claim 1, wherein the (iii) one or more solvents comprises one or more of a glycol ether derivative, a glycol ether ester derivative a carboxylate, a carboxylate of a di-basic acid, a dicarboxylate of a glycol, a hydroxy carboxylate, a ketone ester, an alkyloxycarboxylic acid ester, a ketone derivative, a ketone ether derivative, a ketone alcohol derivative, an amide derivative and mixtures thereof.

13. The formulation of claim 1, wherein the (i i) one or more solvents comprises a glycolic derivative.

14. The formulation of claim 1, wherein the (i) one or more solvents comprises a glycolic derivative one or more solvents selected from the group of ethylene glycol, propylene glycol, propylene glycol monomethyl ether acetate (PGMEA), propylene glycol methyl ether (PGME), dipropylene glycol monomethyl ether (DPGME) and mixtures thereof.

15. The formulation of claim 1, wherein the (iii) one or more solvents comprises, propylene glycol monomethyl ether acetate (PGMEA).

16. The formulation of claim 1, wherein the (iii) one or more solvents comprises propyleneglycol monomethylether (PGME).

17. The formulation of claim 1, wherein the (iii) one or more solvents comprises a mixture of propylene glycol monomethyl ether acetate (PGMEA) and propyleneglycol monomethylether (PGME).

18. The formulation of claim 1, wherein the formulation comprises about 70 wt % to about 98 wt % of the one or more solvents.

19. The formulation of claim 1, wherein the one or more surfactant comprises an organosiloxane polymer.

20. The formulation of claim 1, wherein the formulation comprises about 0.001 wt % to about 5 wt % of the one or more surfactant.

21. The formulation of claim 1, wherein the one or more water resistivity enhancer comprises one or more of propionic acid, n-butyric acid, isobutyric acid, t-butylacetic acid, pentanoic acid, hexanoic acid, heptanoic acid, octanoic acid, nonanoic acid, decanoic acid, maleic acid, fumaric acid and combinations thereof.

22. The formulation of claim 1, wherein the one or more water resistivity enhancer comprises propionic acid.

23. The formulation of claim 1, wherein the one or more water resistivity enhancer comprises isobutyric acid.

24. The formulation of claim 1, wherein the formulation comprises about 1 wt % to about 15 wt % of the one or more water resistivity enhancer.

* * * * *